(12) United States Patent
Dixon

(10) Patent No.: US 7,695,486 B2
(45) Date of Patent: Apr. 13, 2010

(54) INTRADERMAL COLOR INTRODUCING NEEDLE DEVICE, AND APPARATUS AND METHOD INVOLVING THE SAME

(76) Inventor: Linda Dixon, 1569 Aalapapa Dr., Kailua, HI (US) 96734

( * ) Notice: Subject to any disclaimer, the term of this patent is extended or adjusted under 35 U.S.C. 154(b) by 1916 days.

(21) Appl. No.: 10/677,115

(22) Filed: Oct. 2, 2003

(65) Prior Publication Data

US 2004/0116953 A1 Jun. 17, 2004

Related U.S. Application Data

(60) Provisional application No. 60/415,142, filed on Oct. 2, 2002.

(51) Int. Cl.
*A61B 17/34* (2006.01)
(52) U.S. Cl. ................................. 606/186
(58) Field of Classification Search ............. 81/9.22; 112/163; 606/186, 116, 222, 223
See application file for complete search history.

(56) References Cited

U.S. PATENT DOCUMENTS

| | | | | |
|---|---|---|---|---|
| 2,840,076 A | * | 6/1958 | Robbins | 604/46 |
| 3,540,447 A | * | 11/1970 | Howe | 604/165.02 |
| 3,685,101 A | * | 8/1972 | Egerer | 19/129 R |
| 3,872,730 A | * | 3/1975 | Ringrose et al. | 73/864.23 |
| 4,109,655 A | * | 8/1978 | Chacornac | 604/47 |
| 4,508,106 A | * | 4/1985 | Angres | 128/898 |
| 4,582,060 A | | 4/1986 | Bailey | |
| 4,644,952 A | | 2/1987 | Patips et al. | |
| 4,655,912 A | | 4/1987 | Bradley et al. | |
| 4,671,277 A | | 6/1987 | Beuchat | |
| 4,719,825 A | | 1/1988 | LaHaye et al. | |
| D294,519 S | | 3/1988 | Hardy, Jr. | |
| 4,798,582 A | * | 1/1989 | Sarath et al. | 604/47 |
| 4,844,065 A | | 7/1989 | Faulkner | |
| 5,279,552 A | | 1/1994 | Magnet | |
| 5,445,611 A | | 8/1995 | Eppstein et al. | |
| 5,457,041 A | * | 10/1995 | Ginaven et al. | 435/455 |
| 5,785,680 A | * | 7/1998 | Niezink et al. | 604/57 |
| 5,800,445 A | * | 9/1998 | Ratcliff et al. | 606/116 |
| 5,810,862 A | | 9/1998 | Pilamanis | |

(Continued)

FOREIGN PATENT DOCUMENTS

DE 103 43 590 A1 4/2005

(Continued)

OTHER PUBLICATIONS

"The Manufacture of Needles Specifically for Tattooing" © Eikon Devices Inc., Oct. 1995 with Jun. 1996 revisions.

(Continued)

*Primary Examiner*—Kevin T Truong
(74) *Attorney, Agent, or Firm*—Smith, Gambrell & Russell, LLP

(57) ABSTRACT

A needle device having a plurality of needles with applied tips arranged so as to define a plurality of contact edges. In one embodiment one or more oblique edges is provided relative to an intermediate horizontal edge or a plurality of oblique edges with adjacent edges sharing a common needle point vertex. The number and needle grading (e.g., fine/sharper tips; medium and heavy grades) are represented by the different contact edges of the needle device. The number of each needle sub-sets is also preferably varied to provide enhanced flexibility as the application as in cosmetic tattooing. A tool for supporting is also preferably provided as in a reciprocating needle device support is provided. The needle device is particularly well suited for providing permanent eye liner makeup in view of its adaptability to accommodate different skin textures and skin surface presentations.

50 Claims, 16 Drawing Sheets

| | | | | |
|---|---|---|---|---|
| 5,931,794 | A * | 8/1999 | Pitesky | 600/556 |
| 6,030,404 | A * | 2/2000 | Lawson et al. | 606/186 |
| 6,197,034 | B1 | 3/2001 | Gvozdic et al. | |
| 6,206,270 | B1 * | 3/2001 | Huang | 228/138 |
| 6,345,553 | B1 * | 2/2002 | Adler et al. | 81/9.22 |
| 6,456,278 | B1 * | 9/2002 | Lee | 345/168 |
| 6,588,301 | B1 * | 7/2003 | Chanet et al. | 81/9.22 |
| 2001/0027328 | A1 * | 10/2001 | Lum et al. | 606/186 |
| 2001/0034534 | A1 * | 10/2001 | Transue | 606/186 |
| 2005/0066775 | A1 | 3/2005 | Chen | |

FOREIGN PATENT DOCUMENTS

| | | |
|---|---|---|
| JP | 2000-177289 | 6/2000 |
| JP | 2000-342332 | 12/2000 |
| JP | 2001-293095 | 10/2001 |
| WO | WO 03/003821 | 1/2003 |

OTHER PUBLICATIONS

"New Issues & Alerts" AAM Expo 2003, pulled from internet http://www.micropigmentation.org/new%20issues.htm (Apr. 10, 2003).

INRAD® AccuCore™ Single Action Biopsy Needles, pulled from internet http://www.inrad-inc.com/accucore.htm (Sep. 23, 2003).

Pulled from internet http://www.medium-tech.de/images/products/products/english/module.jpg (Sep. 29, 2003) (1 page).

Pulled from internet http://www.medium-tech.de/images/products/products/hygienemodul_big.jpg (Sep. 29, 2003) (1 page).

"MediUm-Tech" Medizingeräte GmbH, pulled from internet http://www.medium-tech.de/english/ (Sep. 29, 2003).

"MediUm-Tech" Medizingeräte GmbH, pulled from internet http://www.medium-tech.de/english/produkte/permanent_makeup/index.html (Sep. 29, 2003).

"MediUm-Tech" Medizingeräte GmbH, pulled from internet http://www.medium-tech.de/english/produkte/permanent_makeup/grundlagen_2.html (Sep. 29, 2003).

"MediUm-Tech" Medizingeräte GmbH, pulled from internet http://www.medium-tech.de/english/produkte/permanent_makeup/grundlagen_3.html (Sep. 29, 2003).

"MediUm-Tech" Medizingeräte GmbH, pulled from internet http://www.medium-tech.de/english/produkte/permanent_makeup/grundlagen_4.html (Sep. 29, 2003).

"MediUm-Tech" Medizingeräte GmbH, pulled from internet http://www.medium-tech.de/english/produkte/permanent_makeup/grundlagen_5.html (Sep. 29, 2003).

"MediUm-Tech" Medizingeräte GmbH, pulled from internet http://www.medium-tech.de/english/produkte/permanent_makeup/sicherheit/index.html (Sep. 29, 2003), 6 pages.

"MediUm-Tech" Medizingeräte GmbH, pulled from internet http://www.medium-tech.de/english/produkte/permanent_makeup/handstueck/index.html(Sep. 29, 2003), 2 pages.

"MediUm-Tech" Medizingeräte GmbH, pulled from internet http://www.medium-tech.de/english/produkte/permanent_makeup/steuergeraet/index (Sep. 29, 2003), 2 pages.

"MediUm-Tech" Medizingeräte GmbH, pulled from internet http://www.medium-tech.de/english/produkte/permanent_makeup/pigmentfarben/inde.. (Sep. 29, 2003), 4 pages.

"MediUm-Tech" Medizingeräte GmbH, pulled from internet http://www.medium-tech.de/english/produkte/permanent_makeup/studie/index.html (Sep. 29, 2003).

"MediUm-Tech" Medizingeräte GmbH, pulled from internet http://www.medium-tech.de/english/produkte/permanent_makeup/studie_2.html (Sep. 29, 2003).

"MediUm-Tech" Medizingeräte GmbH, pulled from internet http://www.medium-tech.de/english/produkte/permanent_makeup/studie_3.html (Sep. 29, 2003).

"MediUm-Tech" Medizingeräte GmbH, pulled from internet http://www.medium-tech.de/english/produkte/permanent_makeup/studie_4.html (Sep. 29, 2003).

Permanent Makeup Products, Services and Education, pulled from internet at http://www.dermagraphicsinc.com/ on Dec. 20, 2004, (3 pages).

SofTap Permanent Cosmetics, pulled from internet at http://www.softaps.com/needles.html?SOFTAPS_Session=b3ef597c4141bdc41ce8392c4.on Dec. 20, 2004 (5 pages).

* cited by examiner

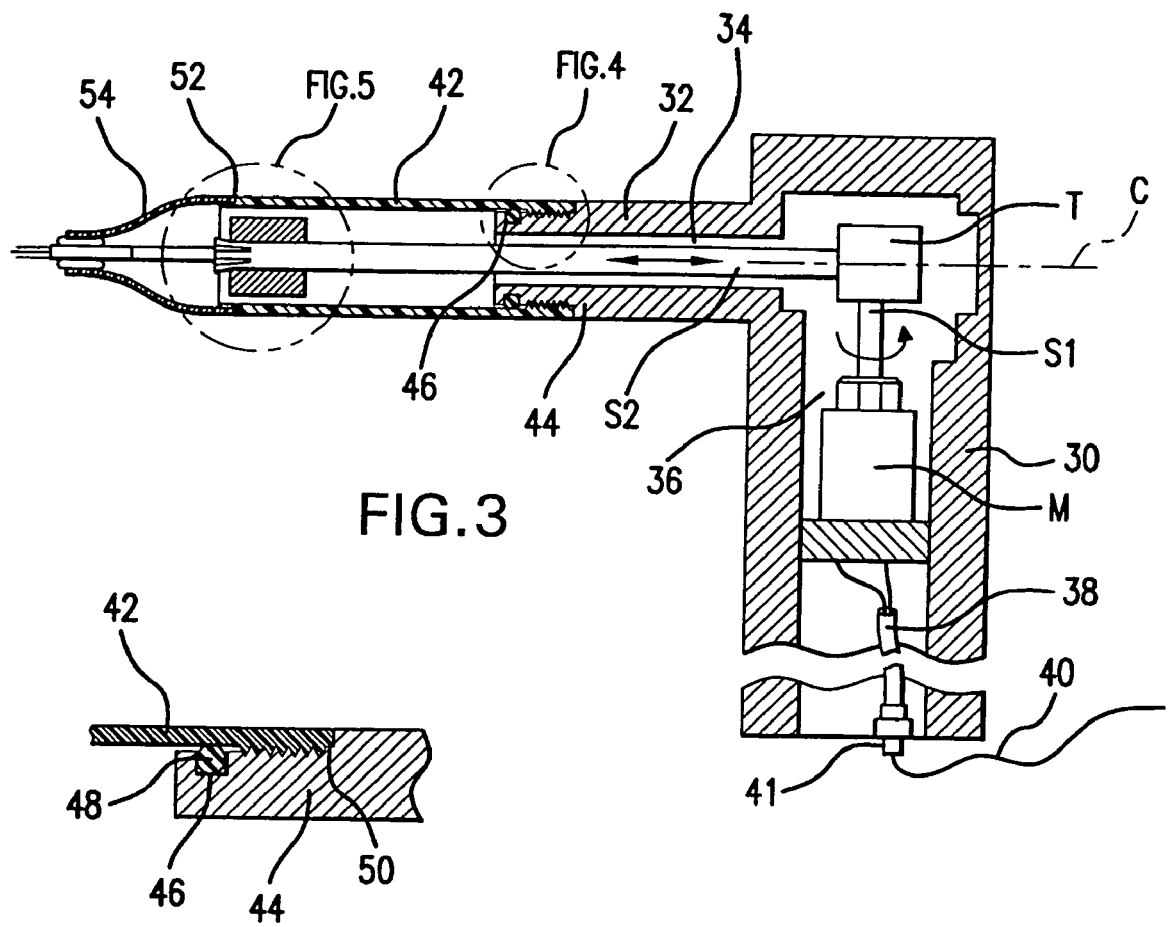
FIG.3
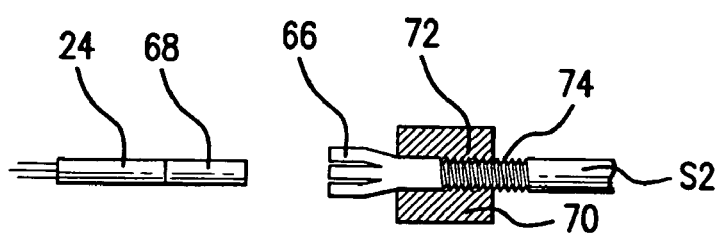
FIG.4
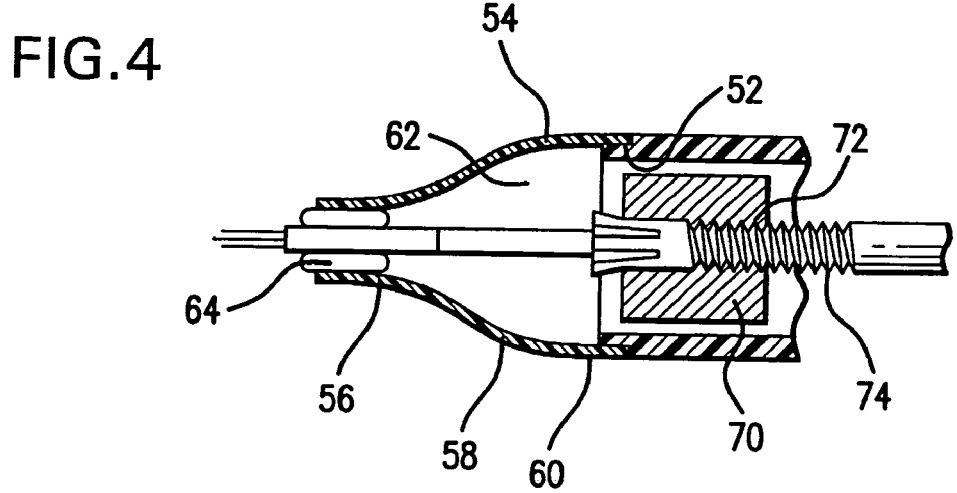
FIG.5A
FIG.5B

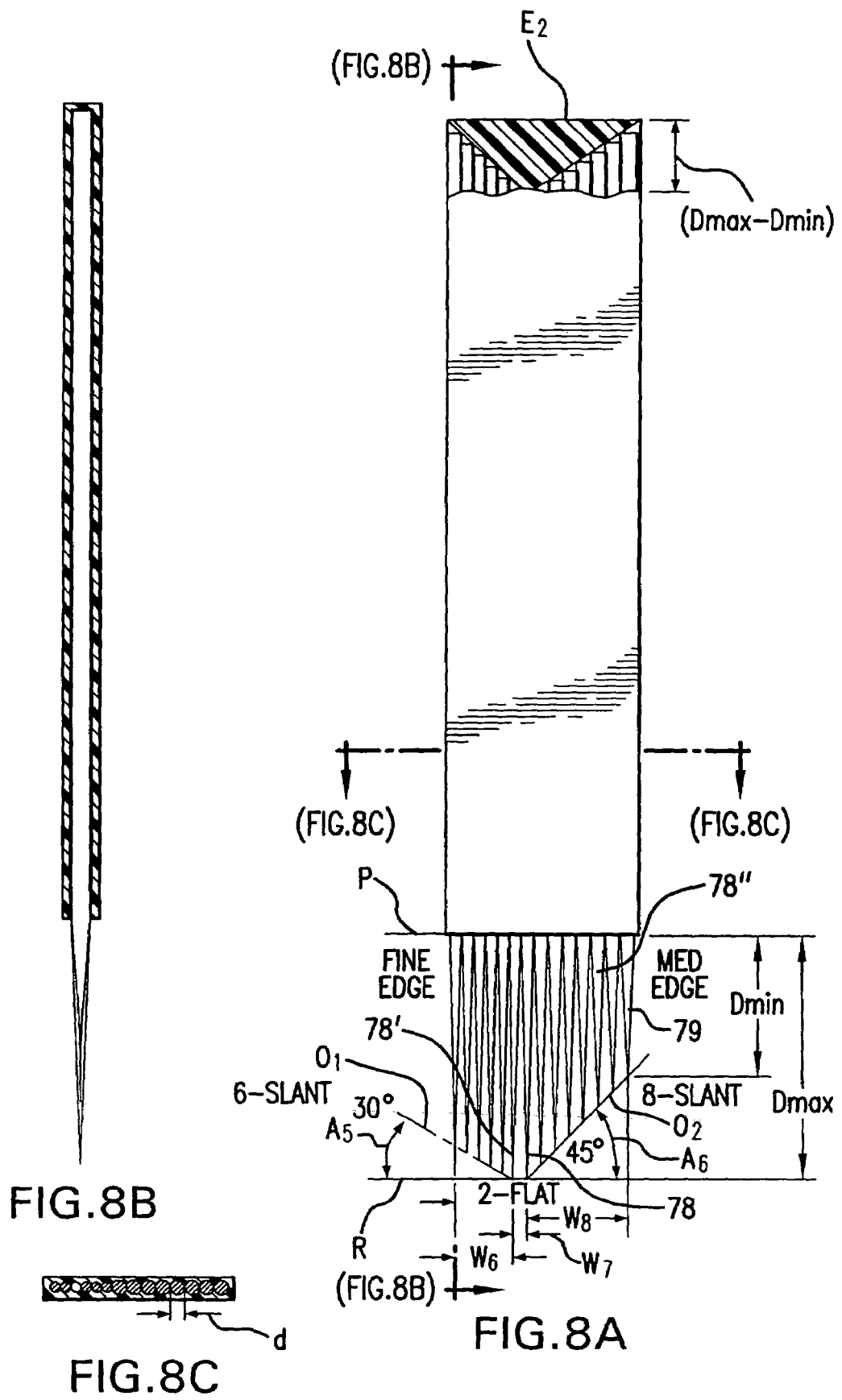

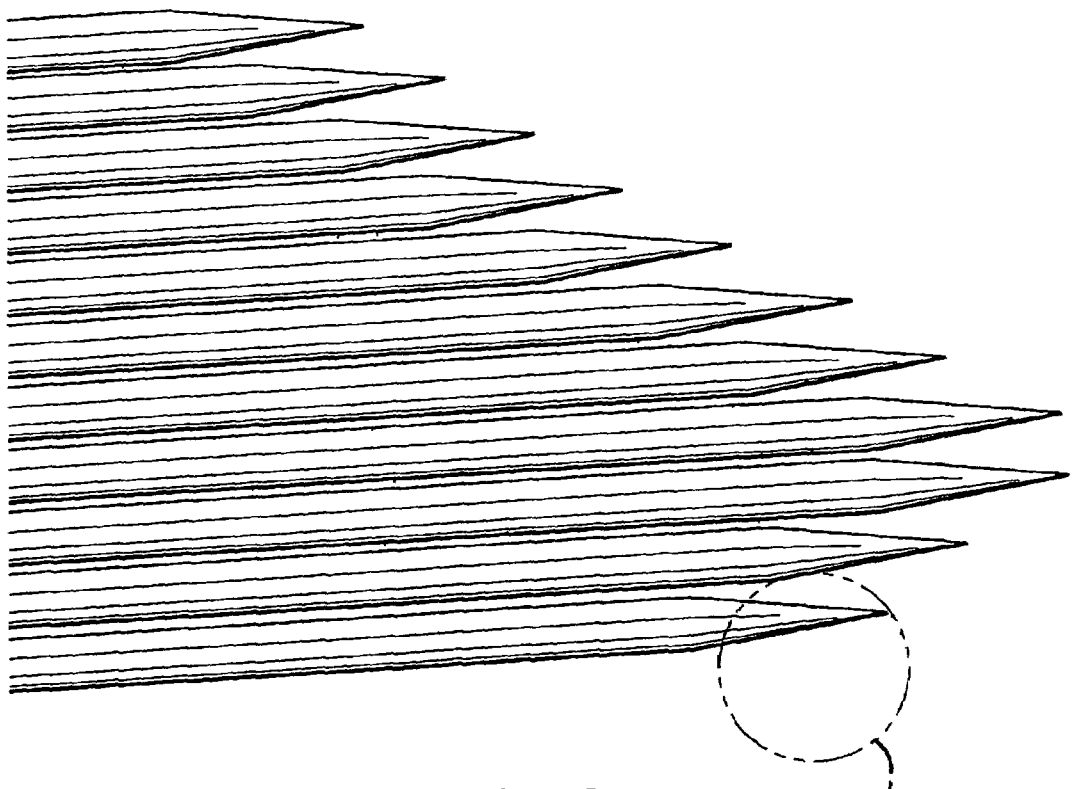
FIG.17A
FIG.17B
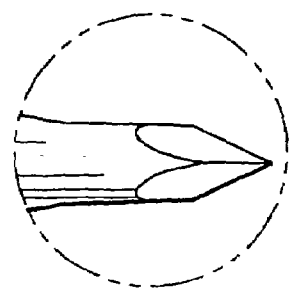
FIG.17B

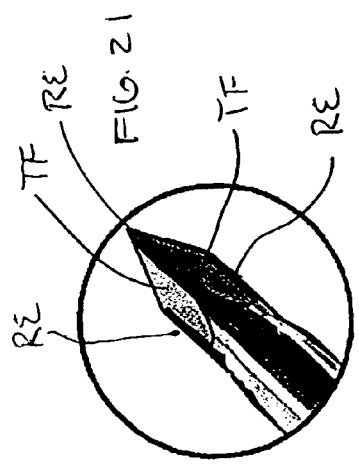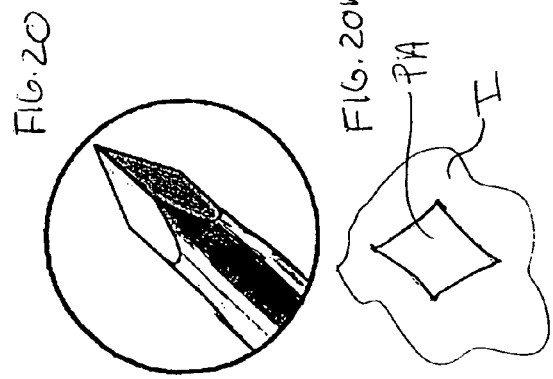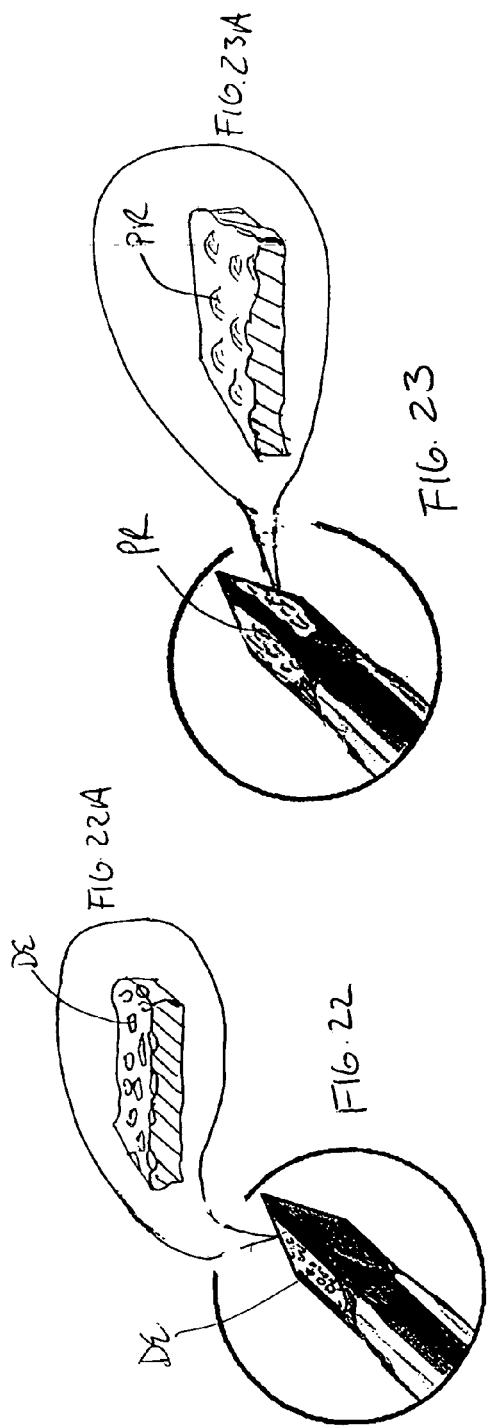

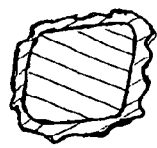
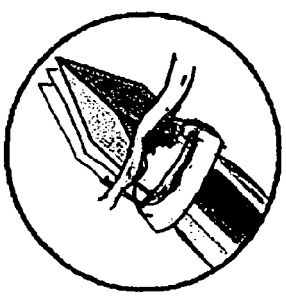
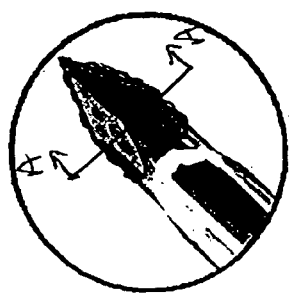
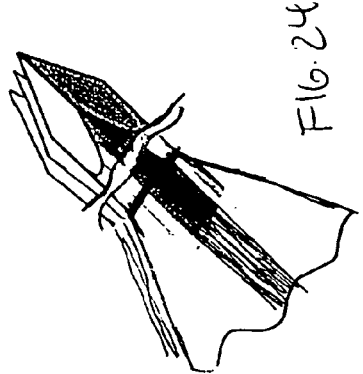
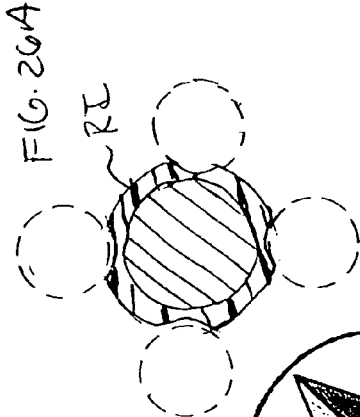
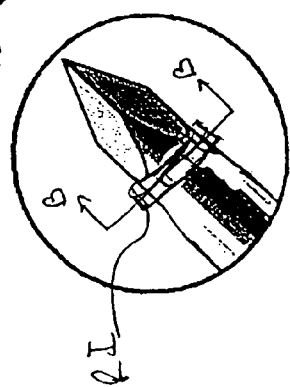

INTRADERMAL COLOR INTRODUCING NEEDLE DEVICE, AND APPARATUS AND METHOD INVOLVING THE SAME

CROSS REFERENCE

This application claims priority from U.S. Provisional Application Ser. No. 60/415,142, filed Oct. 2, 2002.

FIELD OF THE INVENTION

The present invention pertains to a needle device suitable for use in intradermal color introduction as in a tattooing procedure as well as an implementing apparatus and method of using each as in, for example, a permanent makeup providing procedure, and a method of manufacturing the needle device.

BACKGROUND OF THE INVENTION

For centuries efforts have been made to achieve enhanced coloration of skin for a myriad of reasons. Historically, a variety of implements have been used to indelibly color the skin, ranging from sharply pointed bones, teeth, thorns, guitar strings, safety pins, wood, plastic or any metallic object sufficient to penetrate the skin with color so as to leave a visible mark. These colorful or black and white marks, also known as tattoos, have been applied for adornment, symbolic, patriotic, ethnic or religious identification and artistic expression on a human canvas of skin. Interest also exists in the area of cosmetic, corrective or camouflage tattooing (medical micropigmentation) as a method to provide, for example, permanent makeup, or restore color and/or symmetry to the eyebrows, lips, eyelids, breasts, scars and skin conditions from losses suffered by aging, birth defects (cleft lip), cancer treatment (alopecia) or skin changes (hypopigmentation-vitiligo).

Tools to implement a desired intradermal, coloration of the skin with a penetration implement have also evolved over the years. These include early hand tools such as bamboo sticks with strapped needles (a technique still common today in parts of Asia) and motor driven intradermal injection devices. These devices are relied on to inject ink, dye or other marking material (referred to hereafter collectively as "ink" for brevity) just under the skin, so that the ink is retained within the skin and the color of the ink injection pattern is visible. The motorized devices normally comprise a skin-penetrating needle which has the capacity to retain some quantity of ink, a mechanism to reciprocate the needle for repeated punctures of the skin to implant the ink under the skin in the desired pattern, and a housing for the device which the operator holds and often uses to guide the device. There is also typically an off-on switch and power source for the reciprocating drive mechanism. With some devices the operator repeatedly dips the needle into an ink pool to coat the needle, while other devices have built-in reservoirs for the ink from which the ink is fed continuously to the needle.

A number of different devices, particularly with different types of reciprocating needle drives, have been disclosed over the years. Typical of such devices are those described in U.S. Pat. No. 2,840,076 (Robbins: 1976); U.S. Pat. No. 4,508,106 (Angres: 1985); U.S. Pat. No. 4,644,952 (Patips et al.: 1987); U.S. Pat. No. 4,798,582 (Sarath et al.: 1989); and U.S. Pat. No. 5,279,552 (Magnet: 1984).

Examples of pen like (non-motorized) skin marking devices can be seen in U.S. Pat. No. 4,655,912 (Burton: 1987) and U.S. Pat. No. 5,810,862 (Pilamanis: 1998).

Intradermal pigment injection instruments or implements include the use of singular needles. Multi-tip array needles are also featured in the above noted Angres, Pilmanis, and Sarath patents as well as in U.S. Pat. No. 6,030,404 (Lawson et al.: 2000). Reference is also made to the technical report "The Manufacture of Needle Specifically For Tattooing"© Eikon Device Inc., October 1995 with June 1996 revisions, which report is incorporated herein by reference. The needles are designed for penetrating the skin to deliver the ink with the depth being based on insertion depth which, in turn, is dependent upon a variety of factors including the taper and/or diameter of the penetrating needle, the resistance level of the material being penetrated (e.g., the toughness of the skin) as well as environmental factors such as the dryness of the needle and/or skin being penetrated and whether there is wetting or lubrication material on the needle or on the skin being penetrated (or other body material). The invention can also be used for other medical, non-skin use such as medical pigment application to non-skin areas like the cornea of an eye, although the preferred usage and many of the parameters set forth herein are directed at skin penetration.

The age of the person can have an influence on the resistance level to penetration as aging skin tends to lose in collagen level and turgor so as to become more resistant to needle penetration and is also more susceptible to tissue damage from tattoo needles. One's skin also typically becomes thinner than in one's youth, thus playing a role relative to ink penetration levels.

"Single point" needles are typically relatively larger needles that are designed and used alone relative to the holder for line generation (e.g., single line or areas following extensive multiple line repetition). In view of their size, these single point needles typically are more traumatic on the skin leading to greater puffing etc., which can make ink application more difficult and less error free (e.g., if puffing and distortion initiates while the ink application is ongoing in the same area). Single point needles do allow, however, for high definition location application particularly in difficult to reach areas or when attempting to set initial external boundary regions.

Multiple needle configurations such as that described in Lawson are used to penetrate the skin over large areas. They are, however, not always well suited for areas such as those described above where a certain skin topography, desired ink configuration and/or a body arrangement makes the particular array arrangement of the multi-array needles ill suited for a desired use. This entails having to switch out multiple needle types to accommodate the application requirement or the use of a plurality of different holder/needle set combinations.

Furthermore, microscopic examination of tattooed skin to determine the depth and location of ink or colorant means (e.g., particles (pigments)) reveals pigment lying as deep as 2.6 mm in some applications. This depth may be acceptable on some parts of the body, but is excessive on others (e.g., consider the thickness of eyelid skin at 0.5-0.75 mm). Placing colorants too deeply results in skin changes and scarring as well as impaired visibility of the pigment. Considering that, unlike many body tattoos, in excess of 90% of cosmetic tattoos are placed on the face (e.g., eyeliner application) where they are constantly visible without the benefit of a covering (clothes), there exists a particularly high level of concern with respect to the final look and quality of the cosmetic tattoo application. That is, there is little room for visible errors when dealing with cosmetic surgery on the face such as the lips, eyelids, brow, etc. Also, from the foregoing, it is also apparent the putting colorants into the skin is quite variable from a variety of perspectives. This variation is particularly prevalent when dealing with cosmetic surgery on the face where the topography changes and skin texture changes can be more dramatic even in small areas of application. Because of this, there often exists in the prior art techniques a requirement to repeat an application (e.g., eyeliner application repeats) due to poor or improper penetration and/or the providing of insufficient pigment. This is especially undesirable and inefficient in that the initial procedure (which requires a healing process as well) is at least in part a wasted effort.

SUMMARY OF THE INVENTION

The present invention, among other features, facilitates the proper application of an application material (e.g., ink, dye, pigment or other marking including fluid and dry based), thus helping to avoid re-applications. The present invention also helps provide the applicator with greater versatility in the application process which can often provide for efficiencies and a deduction in application time, particularly when dealing with the requirement associated with facial cosmetic applications. The present invention is directed at providing a needle device which implants a large quantity of color with good color reflectance characteristics while lessening trauma to the skin as skin scarring and the like lessens the color presentation.

The present invention also provides for the potential for greater accuracy in application through a high level of instrument adaptation potential for the application areas. This feature is particularly helpful when dealing with cosmetic applications such as eyeliners where the application areas include a wide variety of skin topography and condition changes as well as environment obstructions and avoidance areas (e.g., the eye). Also, the present invention also includes preferred embodiments that lessen the trauma and associated swelling both during and after a procedure so as to facilitate the proper application (e.g., accuracy in both location and depth) of the ink. Through the use of a lubricant such as petroleum jelly applied in conjunction with the potential varied configurations relative to a needle device, there is further facilitated rapid and proper intradermal ink application in even difficult to apply regions. In providing these features under the present invention, there is also lessened the need for repeat applications.

Preferred embodiments of the invention that facilitate providing high quality pigment applications include needle devices which are arranged in sub-sets designed at providing different contact edgings, and/or a needle device comprising integrated fixed sub-sets of different taper and/or gauge as in a finer, medium and/or larger grade needle sub-set arrangements and/or providing needle tip morphology directed at reducing skin trauma and rapid healing promotion while maintaining a high level of surface area for pigment (ink) to needle attachment for intradermal delivery. The needle subsets are provided either in planar fashion "flat" or in alternate groupings including those patterns currently used in the industry but with only one needle type grouping and one surface contact level or edge as in a circular cluster with center tip or a double, stacked row.)

In one embodiment of the invention there is provided a needle device comprising a set of needles each having a non-application end and a pointed application end, the set of needles including a first subset with pointed application ends arranged along a first contact edge and a second subset with pointed application ends arranged along a second contact edge that is non-coincident with the first contact edge. In one embodiment the first contact edge is arranged along a horizontal line when the needle device is vertically oriented, and the second contact edge extends obliquely relative to the first contact edge arranged along the horizontal line. The second contact edge defines, for example an angle of 10° to 60° relative to the horizontal line, or from 20° to 50°, or from 30° to 45°.

Also, in an additional embodiment, the first and second sub-sets of needles are of different grades as in one of the first and second sub-sets having a finer taper than the other of the first and second sub-sets. This includes having the finer taper sub-set of needles with a smaller shaft diameter than the other of the first and second sub-sets.

In further embodiments the first sub-set of needles presents a different number of needle points along the first contact edge relative to the second contact edge, and the first contact edge is arranged along a horizontal line and the second contact edge extends obliquely up away from the horizontal line and has a greater number of needle points than the needle points defining the first contact edge. A preferred ratio range of needle points of the second contact edge relative to the first contact edge is 2/1 to 6/1, or 3/1 to 5/1, or wherein the second contact edge presents 8 needle tips and the first contact edge presents 2 needle tips with each number inclusive of a shared needle point.

An embodiment of the invention also features a first contact edge that extends obliquely up and away from a horizontal reference plane and a second contact edge that extends obliquely up and away from the horizontal plane, as in wherein the first and second contact edges share a common single needle point edge representing a vertex of an angle defined by the obliquely oriented first and second contact edges. The first and second contact edges preferably have a different number of needle points such as the needle points of the first and contact edges being in a ratio of 1.5/1 to 3/1 as wherein the number of needle points defining the first contact edge is 8 and the number of needle points defining the second contact edge is 4 with each inclusive of the common vertex needle point.

In an embodiment of the present invention adjacent needles in the needle set are fixed together and lie in a common plane such as where the needles are fixed together at the non-application ends of the needle set, and free ends of the non-application ends lie along edge lines that are parallel to first and second contact ends.

An alternate embodiment of the invention comprises a third sub-set of needles having pointed application ends arranged non-coincident with respect to the first and second contact edges, as in where the first contact edge is arranged along a horizontal line, the second contact edge extends obliquely up away from the horizontal line to one side of the first contact edge and the third contact edge extends obliviously from the horizontal line to a second side of the first contact edge. The second and third contact edges also preferably have different slope angles (e.g., the second and third contact edges having at least a 10° difference such as wherein the second contact edge has a 30° angle and the third contact edge has a 45° angle).

A further embodiment of the invention features a first contact edge extending along a horizontal line, a second contact edge extending obliquely from a common needle point with the first contact edge and a third contact edge extension obliquely from a common needle point with the first contact edge and having a different slope than the second contact edge and wherein at least two of the first, second and third contact edges present a different number of needle points and/or wherein at least two of the first, second and third contact edges are defined by needles of a different grade, as in wherein each of the first, second and third contact edges are defined by needles of a different grade.

The present invention also includes a colorant implement apparatus, comprising an embodiment of the needle device as described above and a tool to support the needle device such as a tool that includes means for reciprocating the needle.

The present invention also comprises a method of providing intradermal coloring to a recipient, which includes supplying colorant to an embodiment of the needle device described and penetrating a skin region of the recipient to alter coloring of the skin region.

The present invention also features a needle device comprising a set of needles, the set of needles being arranged in a first and second sub-set of needles with the first sub-set having a plurality of needle points arranged along a first line of extension and the second sub-set having a plurality of needle points arranged along a second line of extension non-coincident with the first line of extension as in wherein each of the first and second lines of extension are oblique relative to a horizontal reference plane when the needle device is in a vertical orientation. Also, the needles of the first sub-set are preferably of a different type than that of the second sub-set, and the number of needle points in the first sub-set is preferably different than that in the second sub-set. For example, the first line of extension can be made horizontal and the second line of extension oblique relative to the first line of extension and the second line is defined by a greater number of needle points than that of the first sub-set. Another embodiment of the invention also features the needle points of the second sub-set having a sharper or finer taper than that of the first sub-set.

An embodiment of the present invention also features a plurality of needles arranged in a common plane and fixed in relationship to each other, the needles presenting needle points arranged at different distances from a reference horizontal plane contacting a lower most needle point of the plurality of needles, and the relative distances of the needle points being set so as to provide at least two different non-coincidental needle tip contact sections. For example, a needle device is provided wherein three different non-coincident edges which include non-coincident straight line edges such as a straight horizontal edge and two straight oblique edges.

The present invention also includes a method of forming a needle device, comprising providing a number of individual needles in a side-by-side orientation in a die, adjusting the die so as to present an oblique line of needle points and one other non-coincident edge line of needle points, and fixing the needles in position relative to each other following adjusting the die.

The present invention also features needles that have a non-conical, multi-faceted tip configuration as in a 3 to 10 face trocar needle with taper angles of the border edges of the trocar faces generally conforming to the aforementioned characteristics. In a preferred embodiment the tapering border edges between trocar face surfaces are rounded off which increases the needle tip surface area and avoid too sharp an edge skin cut. Also, to even further increase the surface area and potential retention of ink on the needle (which increases the amount of ink supplied during intradermal insertion) the needle point (trocar, conical, or alternate configuration) is provided with an irregular surface (e.g., a non-polished surface with depressions and/or protrusions).

An embodiment of the invention also features a method and apparatus for forming a multi-faceted needle tip as well as a needle tip having an increased surface area by way of a surface effect (e.g., a non-polished, coarse exposed surface as in a scratched or roughened or convoluted needle point surface etc.), which adds surface texture to a portion or all of the needle point's exposed surface(s). In one embodiment both a surface effect and a desirable tip structural formation (e.g., trocar configuration) are provided with a grinding machine designed to provide, for example, trocar faces (with or without rounded off face border edges) with the ground surfaces being provided with scratched or otherwise irregular surface texture to enhance ink retention on the needle point.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 3 shows a cross-sectional view of the apparatus of FIG. 1;

FIG. 4 shows an enlarged view of the connection of the sleeve to the projection as shown in FIG. 1;

FIG. 5A shows an enlarged view of the needle and chuck of the apparatus of FIG. 1 in a connected state;

FIG. 5B shows an enlarged view of the needle and chuck of the apparatus of FIG. 1 in a separated state;

FIG. 8A shows a shows a third needle tip arrangement of the needle device of the apparatus of FIG. 1 with different grade (e.g. different diameter) needles;

FIG. 8B shows a side view of the needle device of FIG. 8A;

FIG. 8C shows an end view of a needle tip arrangement having subset of needles of different diameters with needles within each subset having substantially the same diameter;

FIG. 17A shows an illustration of the tip end of a needle device of the present invention;

FIG. 17B show a close up view of a trocar tip of one of the needles in a needle device of FIG. 17A and FIGS. 18A and 18B show additional illustrations of flat needle sets under the present invention.

FIG. 20 shows an alternate embodiment multi-faceted needle point configuration of the present invention.

FIG. 20A shows a schematic view of an intradermal puncture pattern produced by the trocar needle in FIG. 20.

FIG. 21 shows another embodiment of a multi-faceted needle point configuration with rounded face border edging.

FIG. 21A shows a schematic view of an intradermal puncture pattern for the needle of FIG. 21.

FIG. 22 shows an alternate embodiment of a multi-faceted needle point configuration with an exposed irregular surface pattern designed to increase the overall surface area of the needle point.

FIG. 22A shows an enlarged view of the recessed, roughened surface pattern for that which is shown in FIG. 22.

FIG. 23 shows another embodiment of a multi-faceted needle point configuration with an (irregular increased area) surface area.

FIG. 23A shows and enlarged view of the raised projection (bulbous in this embodiment) surface area increasing pattern.

FIG. 24 shows an alternate "flat" needle set embodiment with depth penetration control means (shown in cut away to illustrate that the needle point length can be of a varied length (and taper).

FIG. 25 an additional "flat" needle set embodiment with multi-faceted needle tips and with a depth penetration collar feature.

FIG. 26 shows a further embodiment of a needle point with a multi-needle grouping facilitator.

FIG. 26A shows the multi-needle grouping facilitator (taken at the cross-section location B-B) receiving finer gauge needles.

FIG. 27 shows an alternate embodiment of an increased surface area coating over the multi-faceted needle point.

FIG. 27A shows a cross-sectional view taken along line A-A in FIG. 2.

DETAILED DESCRIPTION

Figure 1:
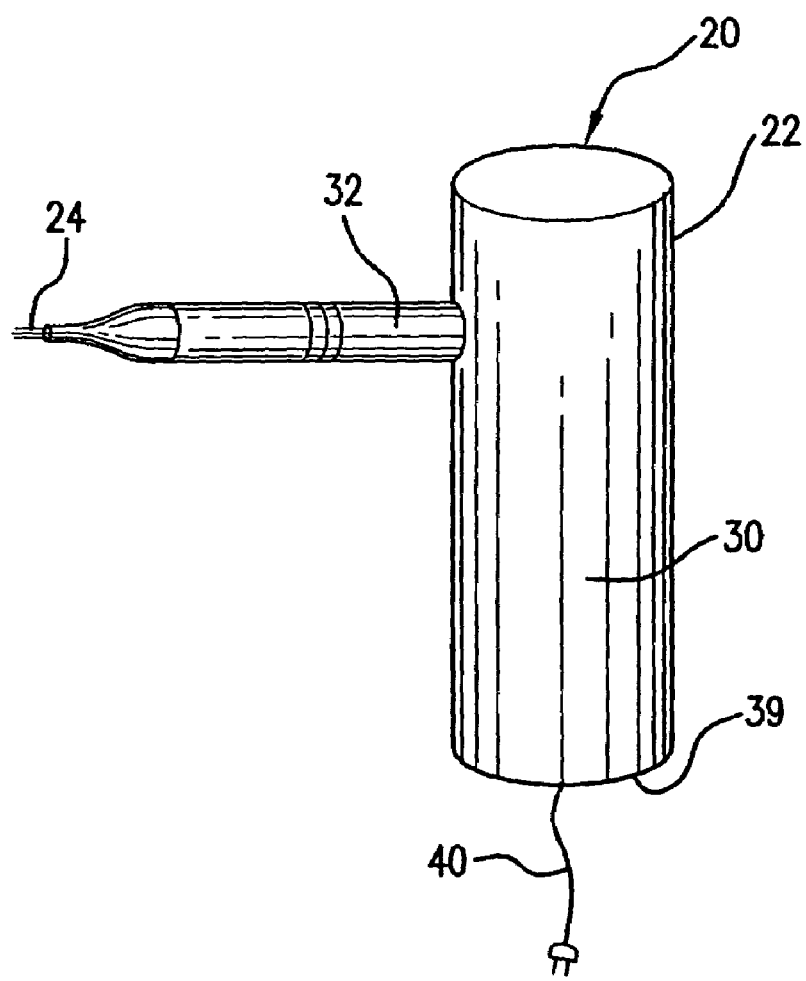
FIG. 1 shows an application implementing apparatus.
Figure 2:
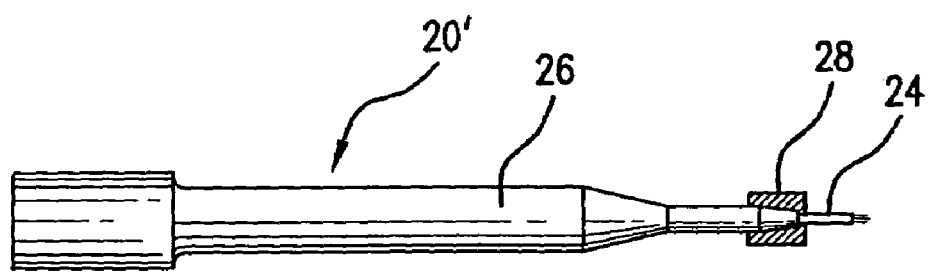
FIG. 2 shows a non-motorized application implementing apparatus.

FIG. 1 provides an illustrative example of an application material implementing apparatus 20 of the present invention which includes a tool or positioning means 22 for positioning a material introducing implement such needle device 24 used in the intradermal application of material such as ink. In FIG. 1, tool 22 is a motor driven intradermal injection device. The tool or means for positioning 22, however, can take on a variety of forms including motorized devices (such as the L shaped device of FIG. 1 or a straight line handle motorized device, not shown). The invention also features non-motorized hand tools such as the FIG. 2 hand tool 20' with handle 26 (with or without a reservoir for the material being supplied). Tool 22 also preferably comprises securement device 28 (e.g., a releasable device as in a removable chuck cap or a permanent securement device such as an adhesive utilized with a disposable (e.g., plastic) handle 26). As will become more apparent below, a motor driven intradermal injection device compliments the features of the preferred embodiments for needle device 24 and, thus, is a preferred embodiment in many circumstances.

With reference to FIGS. 1, 3, 4, 5A and 5B, there is shown an example of implementing apparatus 20 with motor driven intradermal injection device 22. In FIG. 1, injection device 22 includes housing 30 which also serves as a suitable gripping handle for an operator of the device. Injection device 22 further includes projection 32 which extends from housing 30 and features internal passageway 34 (FIG. 3). Housing 30 is provided with an internal chamber 36 within which motor M and transmission T are provided. In a preferred embodiment shaft S1 is rotated by motor M and transmission T includes a motive coupling that converts the rotation of shaft S1 into linear reciprocation of shaft S2 along center line C. Passageway 34 also preferably extends along center line C together with shaft S2. Examples of suitable motive couplings can be seen, for example, in the aforementioned U.S. Pat. No. 5,279,552 and in U.S. Pat. No. 4,582,060 (Bailey 1986) designed to achieve reciprocation of the shaft S2 of, for example, 15,000 cycles per minute. Electrical cable 38 extends from motor M outward to the base end 39 preferably to a plug-in reception jack 41 for line cable 40 with a plug extension at one end for reception in the reception jack (or as another preferred alternative, there is featured a direct continuation of cable 38 directly to the motor in a non-plug in reception jack embodiment).

With reference to FIGS. 3 and 4, there is shown sleeve 42 extending axially away from projection 32. Sleeve 42 is shown connected to the free end 44 of projection 32 and is of a length (e.g., 1 to 5 inches) which helps separate in distance the internal passageway 34 and chamber 36 of the housing from the area of material injection (e.g., ink). Sleeve 42 is also shown in FIGS. 1 and 3 to be cylindrical for preferably over half of its length with a minor convergence in its end farthest removed from free end 44 of projection 32. In a preferred embodiment, free end 44 includes an annular external recess ring 46 (FIG. 4) which receives a seal 48 such as the illustrated O-ring 48. Free end 44 also preferably includes, proximal to the seal 48, step down threaded section 50 onto which interior threads 51 of sleeve 42 are threaded when sleeve 42 is mounted on free end 44. Seal 48 helps avoid any external to internal flow of fluid (e.g., a blood and ink mix) back into passageway 34. Sleeve 42 is a metal sleeve (e.g., aluminum, which is also suitable for housing 30) or in a more preferred embodiment (in view of the potential for fluid contact exposure of sleeve 42), sleeve 42 is a disposable sleeve formed of, for example, a medical grade plastic such as polyethylene. While other releasable attachment means are possible, the threaded connection provides an added degree of versatility in providing an operator with one possible adjustment means wherein the operator can adjust the axial position of distal sleeve end 52 (which influences the relative distance between the application end of needle device 24 and the distal end of tip 54 and potentially the ink needle wetting characteristics). Sleeve 42 is preferably also elongated such as a 1 to 4 inch length.

As shown in FIGS. 3, 5A and 5B, tip 54 has a narrow distal end 56 preferably cylindrical in shape (with a circular or rectangular cross-sectioned passageway through which the needle device 24, which is also preferably planar, on opposite sides extends). Distal end 56 extends to divergent section 58 that opens into larger connection end 60 larger connection end preferably is connected to end 52 of sleeve 42 by way of a friction fit (e.g., a stepped shoulder in end 52 with connecting end 60 sliding over as shown in FIG. 5A or a friction fit sloped slide contact arrangement), for example. In a preferred embodiment, tip 54 is of a translucent or transparent material formed of, for example, a clear plastic (e.g., transparent or at least translucent such as the medical grade plastic noted above) which enables an operator to visualize the interior region 62 which includes the capillary passageway provided by the cylindrical narrow distal end 56 (shown holding, through fluid surface adhesion, dipped ink 64 in FIG. 5A) and the needle and its connection to a support. This material, like the above noted plastic sleeve embodiment, is also well suited for providing a disposable tip which can be supplied in sterile packaging prior to use. Also, the ink can be derived from an interior source in implementing apparatus 20 with a feed to distal end 56.

FIGS. 3, 5A and 5B also illustrate an example of the mounting of needle device 24 through use of, for example, an adjustable (e.g., compressible) chuck end 66 (e.g., three shaft sections defining a suitable reception port for the non-needle tip end 68 of needle device 24). Threaded collet collar 70 extends along shaft S2 and has threaded section 72 which is in threaded engagement with exterior threaded section 74 on shaft S2. As shown in FIG. 5B, the non-needle end 68 of needle device 24 is insertable into chuck end 66, and collar 70 is threaded into a compression needle device locking state as illustrated in FIG. 5A. Other locking means such as threaded, mechanical clamps, key slot, magnetic slot connector, banding, etc. for locking in position the needle device relative to the tool is also encompassed by the present invention.

Figure 6A:
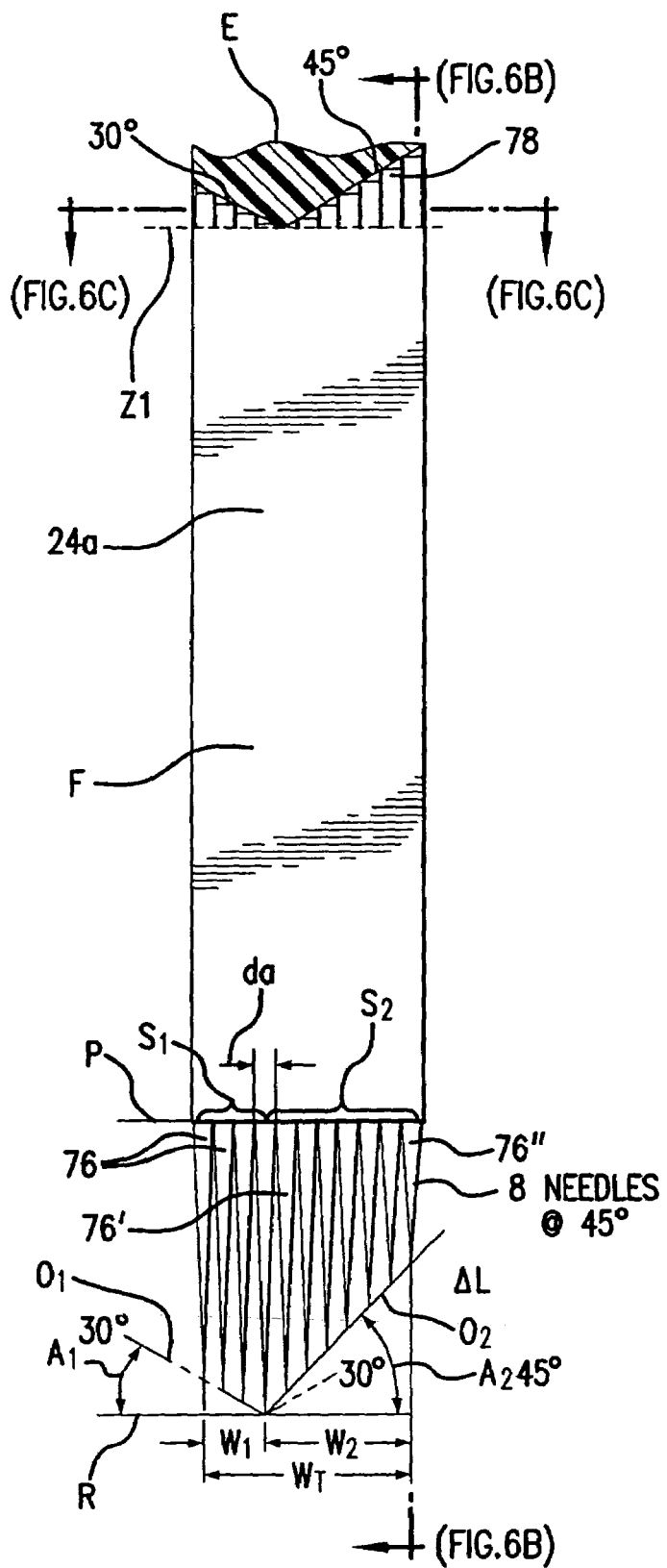
FIG. 6A shows a first needle tip arrangement of the needle device of the apparatus of FIG. 1 and showing the needle device having a non-linear solder.
Figure 6B:
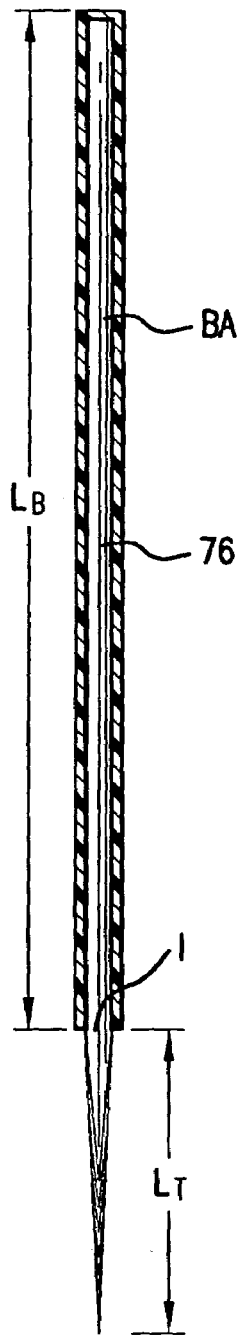
FIG. 6B shows a side view of the needle device of FIG. 6A.
Figure 6C:
FIG. 6C shows an end view of the needle device showing multiple needles having substantially the same diameter (some not shown for draftperson's convenience)
Figure 7:
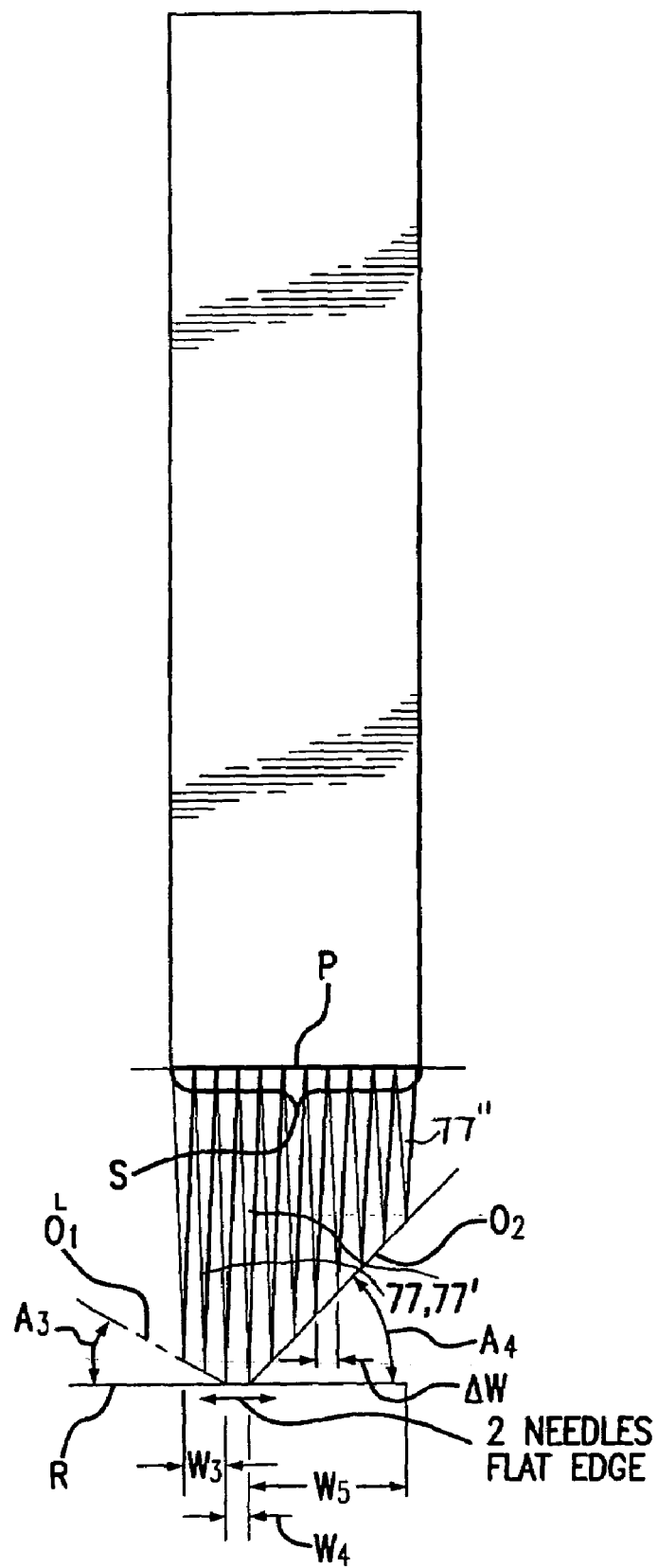
FIG. 7 shows a second needle tip arrangement of the needle device of the apparatus of FIG. 1.

FIGS. 6-8 illustrate some preferred embodiments of the needle device 24 of the present invention which comprise various combinations and configurations of different textured and tapered needles (preferably solid stainless steel) for introducing application material such as colorants into the skin by either manual or machine methods so as to deposit more application material at a desired level with increased versatility and diminished tissue injury. Preferred embodiments of the needle device of the present invention include multiple needles either of the same type or of multiple types all arranged in at least one single planar array or essentially planar array (e.g., deviation of less than 5% relative to an average vertical plane for the needle set or less than 1 mm deviation and more preferably, less than 500 µm deviation). As shown the needles of the needle device extend to different end point locations relative to a common horizontal cross-section reference plane (e.g., plane P in FIG. 6A) of the needle device such that they present a first contact edge extending or arranged along a horizontal line when the needle device is vertical or a first contact point at a horizontal plane from which contact edges slope upwardly away. Multiple single planar array needle sets can also be joined together to form a block of needle set planar arrays (e.g., a matrix) all preferably having tip locations that coincide amongst the needles in the various arrays (e.g., a tip in one array being the same distance away from the reference plane as a coinciding tip in an adjacent array). Because, however, of the versatility provided by even a single needle set array in accordance with the present invention, a single needle set planar array is well suited for many intended uses of the present application without the need for a multiple needle set planar array. That is, the versatility of the present invention is particularly well suited for small, highly varied, and/or difficult to reach areas such as those areas associated with permanent eyeliner application, although the versatility of the present invention can also be taken advantage of in less complex area applications (e.g., shoulder blade or arm). A multiple array block of needle sets in accordance with the present invention (e.g., a 2 or 3 array block) can also, nonetheless, be used for some situations under either of the above noted complex/less-complex application area scenarios.

The needle tip arrangement of a preferred embodiment features a needle set having one or more sub-sets of needle tips in the single needle array with the tips in each needle sub-set preferably positioned to lie along a common line such as an oblique line. Also, the needle type in each sub-set can either have the same characteristics such as surface diameter or gauge, taper and surface characteristics or morphology, or have different characteristics such as varying grades of base diameter and/or taper angles or surface area characteristics.

FIGS. 6, 7 and 8 illustrate a few examples of needle sets under the present invention. The embodiments shown in FIGS. 6-8 are illustrative of needle sets that include a series of needle tips lying on an oblique line $O_1$ which line extends from an end point defined by the intersection of horizontal reference line R and the needle tip of a needle (or needles) extending the farthest distance from plane P. Reference line R is shown, for example, in FIG. 6A as being parallel with the horizontal plane P relative to a vertically oriented needle device 24. The oblique line angle ($A_1$) range for the angle between line $O_1$ and reference line R is preferably 1 to 70°, more preferably, 10° to 60°, and even more preferably 20 to 50° with the angles 30° and 45° being representative of some preferred angles $A_1$ for many applications.

Thus, in one arrangement of the present invention, there is a first sub-set of needles forming an oblique tip line needle sub-set extending from a first exterior side of the needle array of needle device 24 downwardly (relative to a tip down, vertically oriented needle device 24) in sloped fashion along line $O_1$ to a more central region of the needle array, with "essentially" being in reference for example, to less than 5% deviation amongst the tips relative to the desired average oblique line $O_1$, or, alternatively, the applicable manufacturing tolerance range for consistent placement on a desired common line entails. Adjacent the oblique line $O_1$ sub-set of needles is preferably a second sub-set of one or more needles each having a needle tip generally falling on reference line R and in non-oblique fashion if more than one needle is in the second sub-set (e.g., a single needle in the second sub-set not representing a continuous, non-oblique line tip arrangement as in the arrangement shown in FIG. 6A). The needle tip(s) within the second sub-set are preferably arranged along a straight line co-linear with reference line R. For many applications, having all needle tips of a multi-needle second needle sub-set with needle tips falling or essentially falling on a common horizontally oriented reference line R is preferred with "essentially" being used in similar fashion as above.

In the embodiment illustrations of FIGS. 6-8, there is shown the preferable inclusion of a third set of needles having tips lying on a second oblique line $O_2$ (preferably at an angle at least 5° different than the first oblique line set or more preferably with at least a 10° difference such as 30° for one oblique set and 45° for the other set). This third needle sub-set (and second oblique line needle sub-set) has an interior array needle adjacent to (in the case of a single point intermediate between exterior sloping tip lines) or defined by an end needle in the second needle sub-set (when the intermediate sub-set has two or more needle tips) and needle tips running along or essentially along a common oblique line $O_2$ sloping up from the second set to the opposite, second exterior side of the needle array of needle device 24, with "essentially" being used in consistent fashion as above.

Although each of the FIGS. 6-8 embodiments illustrate the preferred double oblique working edge presentation with one or more reference line R positioned needle tips and with the oblique angles preferably arranged to opposite sides of the intermediate sub-set, the present invention also includes a reference line R sub-set with a single oblique sub-set arrangement, such as a first set of non-oblique needles with tips falling along or essentially along common reference line R that is provided together with a single oblique line sub-set preferably positioned to one side of the non-oblique needle set (left or right side when viewing the needle array flush on a common plane).

Each of the above noted sub-sets can all have the same gauge or diameter needle and/or the same taper angle needles across all of the sub-sets such that the versatility of the needle device is based on the different needle tip positioning (oblique and/or straight working edge sets or multiples of the oblique and/or straight sub-sets). The present invention also includes providing different needle gauges or diameters and/or taper angles and/or surface characteristics either within a common needle set and/or from one set to another to provide further needle device versatility. For example, an embodiment featuring a "left side" "fine" edge needle set and a "right side" "medium" or "heavy" edge set either extending to opposite sides from an intermediate single, maximum extension needle or to opposite sides from an intermediate central straight reference R line sub-set of multiple needles is representative. In the latter example, the number of needles in the oblique sets each preferably have a greater number of needles relative to the intermediate straight line sub-set, which greater number is either the same for each oblique sub-set or more preferably a different number (e.g., a ratio of 7/6 to 12/6 preferably favoring the heavier needle set). A "fine", "medium" and "heavy" needle sub-set can be achieved by, for example, using a common diameter needle base but different taper angles (and correspondingly different taper portion lengths). Alternatively, different diameter needle bases with the same or different relative taper angle (and correspondingly different taper lengths) or any combinations of the same are alternatively provided under the present invention. When using different grade levels in a needle set, the grades are preferably represented by base needle diameter ranges of different sizes which provide "fine"; "medium" and "heavy" sizings. The ratio of the number of oblique to non-oblique needles within an array's needle set is preferably 2/1 to 6/1 (more preferably 3/1 to 5/1 and most preferably 4/1) with the minimum number of non-oblique needle(s) preferably being 1 and the preferred upper limit for the oblique set being 12 for most applications. Either a common taper length or different taper length are possible relative to the different sizes noted above with a 0.5 to 1.5 mm taper length range being illustrative, with the taper length being defined by the distance along the central axis of a needle between the taper convergence start location and the needle tip.

Also, FIGS. 6-8 illustrate the extension distance $D_{max}$ (defined by the distance from a needle tip to a cross-section plane P with the plane P extending through the taper initiation location for the needle within the array having a taper initiation location closest to reference line R and referenced in FIG. 8). In a preferred embodiment, the maximum distance D ($D_{max}$ see FIG. 8) ranges from 4 to 20 mm for many applications, more preferably 6 to 16 mm and more preferably 8 to 10 mm. $D_{min}$ represents the minimum needle tip distance from plane P (for the needle set as a whole unless otherwise indicated)—see FIG. 8) amongst the needle set under consideration. $D_{min}$ is preferably 1 to 5 mm less than $D_{max}$.

In a preferred embodiment, each needle sub-set (e.g., an oblique line needle sub-set) has (within the sub-set) a common diameter base, overall axial length, and a common taper length but different extension distance whereby the oblique needle tip series arrangement is achieved by relative axial shifting of one needle in a sub-set next to another whereby the $D_{min}$ needle for that sub-set is spaced from reference R for an amount ($D_{max}$–$D_{min}$). For example, in FIG. 8A there is a far right needle 79 at the extreme of oblique line $O_2$ for the pertinent oblique line needle sub-set and needle 78 represents a needle having a tip on reference line R and also a needle representing the interior end of the oblique line needle sub-set. Thus, the tip of needle 78 is spaced a distance $D_{max}$–$D_{min}$ relative to the tip of needle 79 which defines angle $A_6$ (e.g., 45° 48°) for oblique line $O_2$ in the preferred embodiment, wherein the needles in a sub-set are of a common type and the oblique line of needle tips is achieved by relative (e.g., vertical) shifting of needles within a sub-set. The distance of the upper end of the needle 79 is vertically spaced above the upper end of needle 78 is also equal to $D_{max}$–$D_{min}$ (as shown in the upper region of FIG. 8A). Alternatively, in the needle device manufacturing process, each needle can be pre-designed (e.g., different length bases extending from a common back plane) to achieve the desired needle tip positioning on the working needle device end.

Also, when using the relative shifting technique illustrated in FIGS. 6 to 8, the chucking or connection means for locking in position a needle device to its holder can accommodate uneven back edges produced by, for example, a solder application over the needle bases to the back end (or other needle set holding means). In other words, the holding means can be applied in an intermediate region of the needle device and/or even the uneven edge region so as not to require a planar back end for the needles. For other connection arrangements however, it may be desirable to have a planar back end of the needle device. For example, after achieving the desired needle tip spacing the back end of the needle array can be cut (e.g., along plane $Z_1$, FIG. 6A, representing the upper end of the needle 76' and parallel with plane P) either before or after fixing the needles in position such as by a solder or over molding process like that illustrated in FIG. 8A wherein a plastic covering holds the needles in position and can be readily formed with a planar back wall. Again, however, since the desirable chucking arrangement and other needle device accommodation means provide for the insertion of jagged needle set back end like that represented by non-linear solder in material edge E in FIG. 6B, an arrangement like that shown in FIG. 6B is suitable for many applications under the present invention).

A preferred embodiment features common needle dimensions at least within a common needle sub-set, such that within each sub-set the taper is the same and the taper distance is equal (as shown in FIG. 6C). This facilitates a manufacturing of the needle device 24 whereby a die is provided with a needle tip and or rear end contact oblique and/or straight walls that corresponds with the opposite end needle point edge profile and wherein a solder adhesive or other attachment or bonding application (holding means) is provided to-fix the 25 relative needle positions of the needles in needle device 24 once the die properly positions the needle tips (e.g., an oblique wall surface or a combination straight line/oblique wall or two oblique plane die contact surfaces or combination of the same are placed in contact with the non-pointed ends or the needle tips for final positioning of the needles). In an alternate embodiment, each needle has a common base length (from plane P upward) and the oblique sets are comprised of different length needles taper lengths having different D values ranging from $D_{min}$ to $D_{max}$. If the base of a needle in a set or sub-set is of a common diameter ("d" FIG. 8B) and the taper length is different than, the taper angle varies from needle to needle within the set or sub-set. Alternatively, or in addition, different diameter bases are provided which can influence the taper extension with or without different taper angles. A variety of different combinations involving, for example, taper length, taper angle, and/or base diameter can be utilized to achieve the desired tip locations such as those described above and below. As also described below, the same needle characteristics can be varied to provide different grades of needles such as in one sub-set of needle to another and/or internally within a common needle sub-set. Also, a conical taper arrangement for each needle in a set, or a multi-faceted (e.g., multi-face trocar) taper arrangement for each needle in a set or a combination (e.g, one sub-set with a trocar taper and another one of the noted subsets with a conical taper), are arrangements featured under the present invention.

Reviewing in more detail the needle set devices illustrated in FIGS. 6 to 8, FIG. 6A illustrates a first embodiment example of needle device 24 ("24a" in FIG. 6A) and includes a set of needles 76 (e.g., stainless steel) of a common gauge or diameter "da" in the illustrated embodiment at their pre-taper elongated base section BA (FIG. 6B). Needles 76 also include a ratio of length of taper portion ($L_T$) to length of non-taper portion or elongated base section 78 ($L_B$) or "$L_T/L_B$" (FIG. 6B) of about ⅛ to 1/16, for the illustrated embodiment and which is common for each needle in the needle array (prior to cutting off along plane Z or below if a cutting step is involved). As noted above, this provides for the use of a generic set of needles for each needle array sub-set (e.g., oblique set) and thus can facilitate the providing of and assembling of individual needles within the combined needle device.

In the embodiment shown in FIGS. 6A to 6C, there is a single intermediate needle 76' defining an intermediate needle sub-set which extends the farthest away from plane P. Thus, reference line R is established by needle 76' (relative to the needle device 24 being in a vertical orientation and with R being transverse to a vertical line extending along a center of needle 76'). In a preferred embodiment, two oblique needle tip sub-sets extend along lines $O_1$ and $O_2$ which are arranged obliquely at respective angles $A_1$ and $A_2$ relative to the horizontal reference line R. For the illustrated embodiment of FIG. 6, intermediate needle 76' is offset widthwise such that there is a greater number of needles contacting one or the other opposite side oblique lines $O_1$ and $O_2$ ($O_2$ in the illustrated embodiment) and the angles represented by $A_1$ and $A_2$ are preferably different and, for many applications, $A_1$ is of range of 20° to 60°, more preferably 25° to 45° and with an angle of 30° being particularly well suited for many uses of the present invention. Angle $A_2$ is, for many preferred applications of the present invention, greater than $A_1$ such as by 5-25°; more preferably 10° to 20° and with $A_2$=45° being an example of an angle for $A_2$ which is well suited for many intended uses of the present invention, particularly in conjunction with the above noted preferred ranges for angle $A_1$, and with the single intermediate needle sub-set and two oblique line needle sub-sets to opposite sides thereof embodiment shown (also for the embodiment in FIG. 6|$A_2$-$A_1$| is preferably 0° to 30°. A preferred range of angle difference between $A_1$ and $A_2$ and a difference of 10°-20° being more preferable and with angle differences of 10°, 15° or 20° representing angle difference values well suited under the present invention (although $A_1$=$A_2$ is also a feature of the present invention, but less preferred in not providing as high a degree of versatility needle use).

The number of needle tips falling along $O_1$ is preferably 2 to 10 for many uses of the present invention. A range of 4 to 8 is also well suited for many intended uses of the present invention. The number of tips along oblique line $O_2$ preferably is from 2 to 12 in number for many intended uses of the present invention with a number for 4 to 10 being further illustrative of a preferred range and 5 to 8 being well suited for many uses of the present invention. Having the number of $O_2$ needles greater in number than the needles of $O_1$ is preferred such as a 1 to 10 needle number difference, with a difference of 2-4 being well suited for many uses of the present invention (with $O_2$ at angle $A_2$ preferably having the greater number). A ratio of the number of oblique tips along $O_2$ to the number along $O_1$ (each oblique tip number being inclusive of the intermediate needle 76') is preferably from 5:1 to 1:1 with 8:4 being illustrated in FIG. 6.

Also, as shown in FIG. 6, the overall width of the needle array is $W_T$ which is represented by $W_1+W_2$ with $W_1$ representing the distance between the reference contact point of a vertical extension of the external most needle tip located on line $O_1$ (left most needle in FIG. 6) with reference line R and the intermediate needle 76' tip, and $W_2$ representing the distance between the reference line R contact point of a vertical extension of the external most needle tip located on line $O_2$ (right most in the Figs) and the needle 76' tip (or the one closest to the far edge under consideration if multiple intermediate needle tips are involved).

As shown in FIG. 6A, the distance $W_1$ preferably does not equal $W_2$ such that the tip of the intermediate needle 76' is preferably off-center and, relative to a preferred embodiment, offset so as to have $W_1<W_2$. Examples of $W_T$ values include 2 to 6 mm, and more preferably 2.5 to 5 mm.

Within width $W_T$ the spacing ($\Delta w$) between needle tip locations along line R (actual contact points or extensions relative to reference line R) can be adjusted by altering the taper and/or the needle diameter for each sub-set or for an entire array set of needles. Thus, the relative distance between adjacent needle tips can be the same for the entire width $W_T$ or varied such as a first spacing value for one sub-set and a different spacing value amongst the needles of a second sub-set. The individual needles can be in direct abutment or spaced apart with the holding means and/or spacers being used to keep the desired relative spacing between needles. The above spacing and $\Delta w$ features add versatility with respect to how much ink is held by the needles as more color is available with increased spacing between needles below the base to base contact region (e.g., increasing taper and/or needle diameter). An average needle tip spacing range $\Delta w$ relative to reference line R is preferably from 0.1 to 0.5 of a mm, with 0.3 to 0.4 of a mm being well suited for many preferred uses of the present invention. FIGS. 6 and 7 are illustrative of similarly spaced apart needle tips relative to reference line R. FIG. 8 illustrates another embodiment of the present invention having different grade needles (in this example fine edge and medium edge grades) with the fine edge grade having a smaller diameter different gauge base and/or a different taper angle needle size relative to the medium grade.

The FIG. 6 embodiment features a single needle 76' for its intermediate needle sub-set representing a common vertex for angles A1 and A2. Thus the needle in FIG. 6 provides two working edges to the applicator with one having 4 (inclusive of intermediate needle 76') needle tips (at a 30° slope) and the second working edge having 8 needle tips along its working edge (inclusive of needle 76') at an oblique angle of 45° as well as the single intermediate needle point (at least for some degree of penetration before adjacent needles come into play).

The FIG. 7 embodiment features a three working edge embodiment with two needles 77' for the intermediate needle sub-set having tips contacting reference line R representing the interior working surface. A second working edge is represented by three needles, 77 (three inclusive of one of needles 77')in the intermediate set (the left one in FIG. 7) and at an angle $A_3(=A_1)$. The third working edge is defined by needles 77" in FIG. 7 and includes 9 needles (inclusive of the intermediate right needle 77')at an angle of $A_4(=A_2)$. The distance for $W_3$, $W_4$ and $W_5$ is preferably 25%, 10% and 65% of $W_T$ respectively with the difference providing three distinct working surfaces with different ink insertion characteristics (e.g., different spacing and configuration of the needles and/ or oblique versus non-oblique arrangements and/or working surface width differences and/or different numbers of needles within sub-sets). The intermediate sub-set preferably ranges from the single point to a width $W_4$ of 5-40% while the oblique lines represent (either individually when only single oblique line or in sum when more than one oblique line involved) a preferred range of 50 to 95 whenever a multiple needle tip intermediate needle sub-set is involved.

Thus, the applicator has available different width needle sub-sets that can be switched in use to accommodate different application areas (small, tight application areas versus larger areas better suited for wider width working surfaces) without having to replace needles in use. This also can help avoid the degree of inflammation in the working area as a quicker application is made possible (e.g., 30 minutes for an eyeliner application) which can avoid or minimize application degradation due to a decrease in the needed contact time required. Also, in addition to lessening the required number of contacts and time associated with the number of contacts, the versatility of the present invention also provides for usage of a better suited grade of needle relevant to the current use. For example, the use of well suited working edges such as in the use of (e.g., fine needles) needle sizing and/or the great adaptability of a particular oblique or horizontal working edge relative to the contact area can hold avoid puffing in the application area being worked.

Thus, the present invention provides for different insertion qualities and application (e.g., location use) usage choices based at least in part (relative to same preferred embodiments) on the oblique or non-oblique choices of working edges and the degree of obliqueness of the same. Also, in addition to different width options, there is made available under the present invention different needle tip obliqueness levels relative to a central axis of the needle device. In some instances, an oblique needle tip assertion is desirable in use which in other situations a non-oblique. Also, the degree of obliqueness (e.g., a 45° versus a 30°) provides insertion penetration levels and/or an arrangement better suited for certain contours or handle gripping relative to an application area.

The FIG. 8 embodiment also features a two needle intermediate (straight edge) sub-set with a fine grade (left) and medium grade (right) needle sub-set to opposite sides of the intermediate sub-set which intermediate sub-set can either include, for example, an alternate grade (heavy) or a common grade with one of the two sizes or a hybrid arrangement one fine and one medium consistent with the respective oblique line sub-sets. Thus, there is provided greater control in the application in achieving steadfast color with minimized skin damage in a permanent makeup application (e.g. eyeliner). In such an application, for example, there is provided the flexibility of using one edge type (e.g. an oblique 3 series as in FIG. 7A for tight areas as in the Cupid's Bow or the tail of an eye brow region) wherein fine detail work is possible within these small areas, while for far more opened up areas as in the central brow region, the opposite side with its slope line 8 needle extension, is well suited. Similarly, the multi-edge needle provides for the versatility (e.g., a needle device with 3 working surfaces with two different needle sizes as in medium and fine) of providing one edge with slightly larger needles for the brows where the skin is thicker than the eyelid, while also, with the same needle device, provides for etching in a few ultra-fine hair strokes or eyeliner with the same needle device but with a different, finer gauge needle, for example.

Figure 9A:
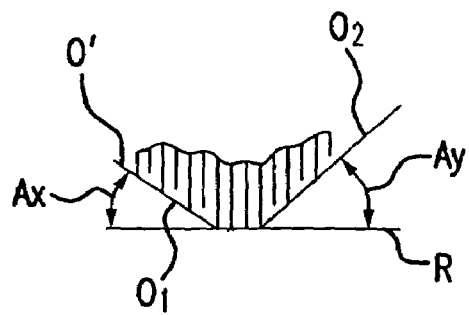
FIGS. 9A-9D schematically show alternative embodiments of the needle tip arrangement.
Figure 9B:
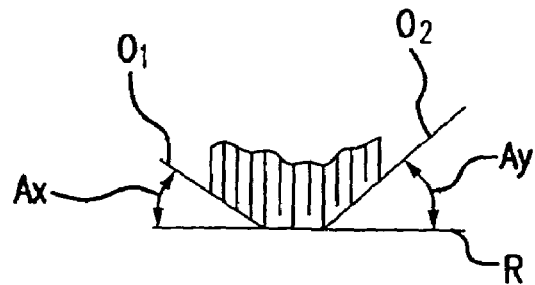
Figure 9C:
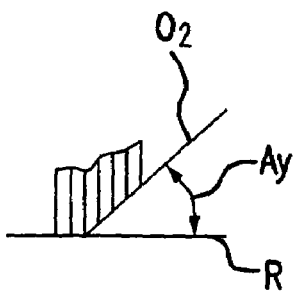

FIGS. 9A-9C illustrate in schematic fashion some alternate embodiments of the present invention. FIG. 9A shows a schematic view of a needle tip arrangement featuring an intermediate zone and two oblique zones ($O_1$, $O_2$) to each side thereof at angles $A_x$ and $A_y$ which are preferably different angles such as those ranges described above. An additional feature illustrated in FIG. 9A is an alternating staggered or saw tooth needle tip arrangement. For example, the two oblique line tip edges $O_1$ and $O_2$ feature tips designed to fall along the noted lines as well as every other needle tip being offset relative thereto (e.g., a 2-10% deviation relative to the conical tip length). With this arrangement, liquid surface adhesion provides for accumulation of liquid between relative tips. In the embodiment shown in FIG. 9A the two side edges have the staggered arrangement, while the central edge has a non-staggered arrangement.

FIG. 9B illustrates an alternate arrangement similar to FIG. 9A but with side edge $O_1$ having a non-staggered relationship while the straight line and oblique linear $O_2$ edges with staggered edging as described above, and with angle $A_y$ in the ranges noted above for the other angles.

Figure 9D:
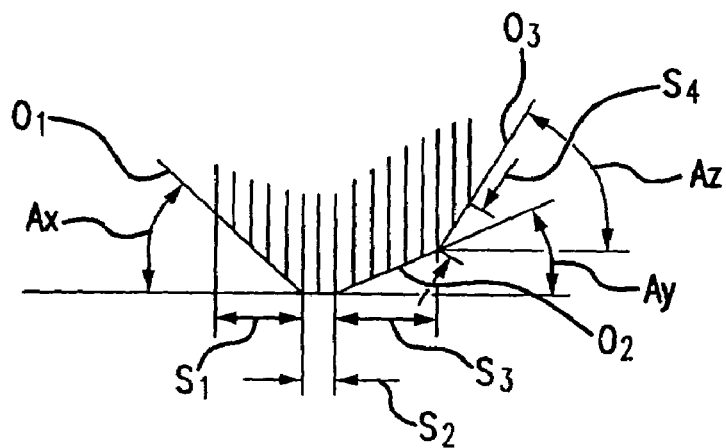

FIG. 9C illustrates an alternate embodiment having a single straight edge and a single oblique edge at angle $A_y$. FIG. 9D shows an additional embodiment featuring four independent side edges $S_1$, $S_2$, $S_3$ and $S_4$ which is an example of a greater than three multiple side edge arrangement featuring oblique edges $O_1$, $O_2$ and $O_3$ with respective angles $A_x$, $A_y$ and $A_z$ with the more external $A_z$ preferably being a greater slope than interior angle $A_y$ and with $A_x$ preferably being different than both $A_z$ and $A_y$ (e.g., an intermediate value $A_y < A_x < A_z$).

Figure 9E:
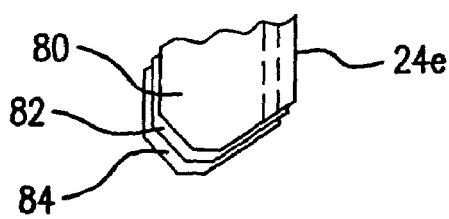
FIG. 9E schematically shows an embodiment of the needle tip arrangement having a multi-array set of needles.
Figure 16:
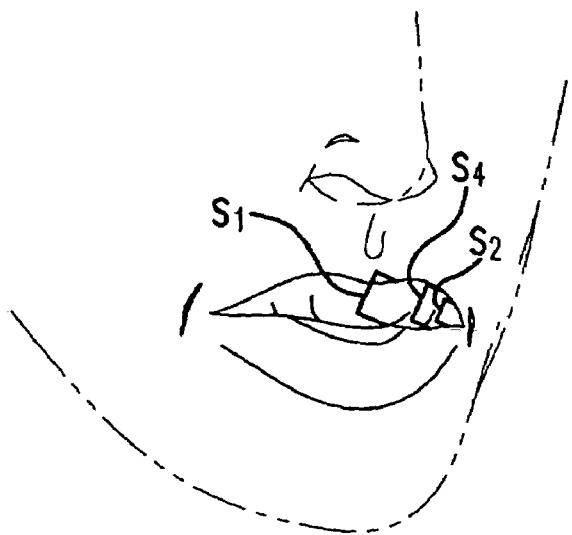
FIG. 16 illustrates lips to be subjected to ink application utilizing a needle device of the present invention such as that shown in FIG. 9D.

FIG. 9E shows schematically needle device 24e represented by a multiple needle array assembly having multiple independent planar needle sets (three in this example as represented by needle sets 80, 82 and 84). The needle sets are preferably arranged so as to coincide (i.e., their needle edge fall on common planes going across laterally positioned needle sets—the illustration in FIG. 9E being in perspective so as to enhance visibility). Thus, needle device 24e features three needle arrays each having a straight edge intermediate needle sub-set and two oblique needle sub-sets to opposite sides of a respective intermediate needle sub-set. With a matrix arrangement such as shown in FIG. 9E, greater area application is achievable upon needle tip contact application while retaining at least to some extent the varied edging availability to promote optimum needle edge to applicable surface contour and accessible area size applications. As an example, FIG. 16 illustrates lips to be subjected to ink application utilizing a needle device of the present invention such as that shown in FIG. 9D. As shown in FIG. 16, across the surface of the lip there is a varying width (as well as varying topography). Thus, for those areas having greater width, a longer edge is often more desirable such as edge $S_1$ of the FIG. 9D set with edge $S_4$ having an intermediate length and incline better suited for an intermediate width area and subset edge $S_2$ better suited still in the narrower region noted for $S_2$. Also, across the wider areas which are generally not highly varying, a multi-array set such as shown in FIG. 9E can be utilized, although it is often preferable to utilize a single array needle device such as the FIGS. 8 and 9A to 9D examples as a single set allows for a single needle device to be used for all or essentially all application area facets while a multi-array set might not be suited for some closer areas (thus resulting in an undesirable switching or alternate tool usage requirement during an application processing).

Figure 15:
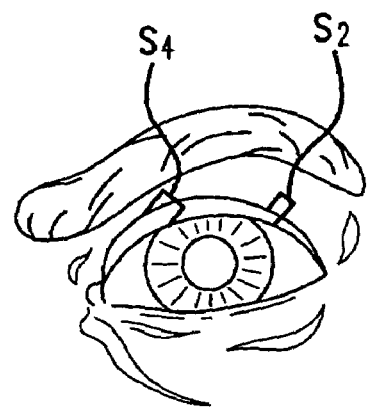
FIG. 15 illustrates an eyelid region of an eye which is to be provided with permanent eyeliner.

FIG. 15 illustrates an eyelid region of an eye which is to be provided with permanent eyeliner (typically would be stretched further by the applier through finger contact or via a stretch tool such as illustrated in U.S. Pat. No. 4,506,106 to provide both a wider and flatter working surface). As seen in FIG. 15, the region is relatively narrower such that the usage of the shorter length needle sub-sets $S_4$ and $S_2$ (upon the operator merely manipulating the tool position) are utilized in the relatively different width areas.

Figure 10:
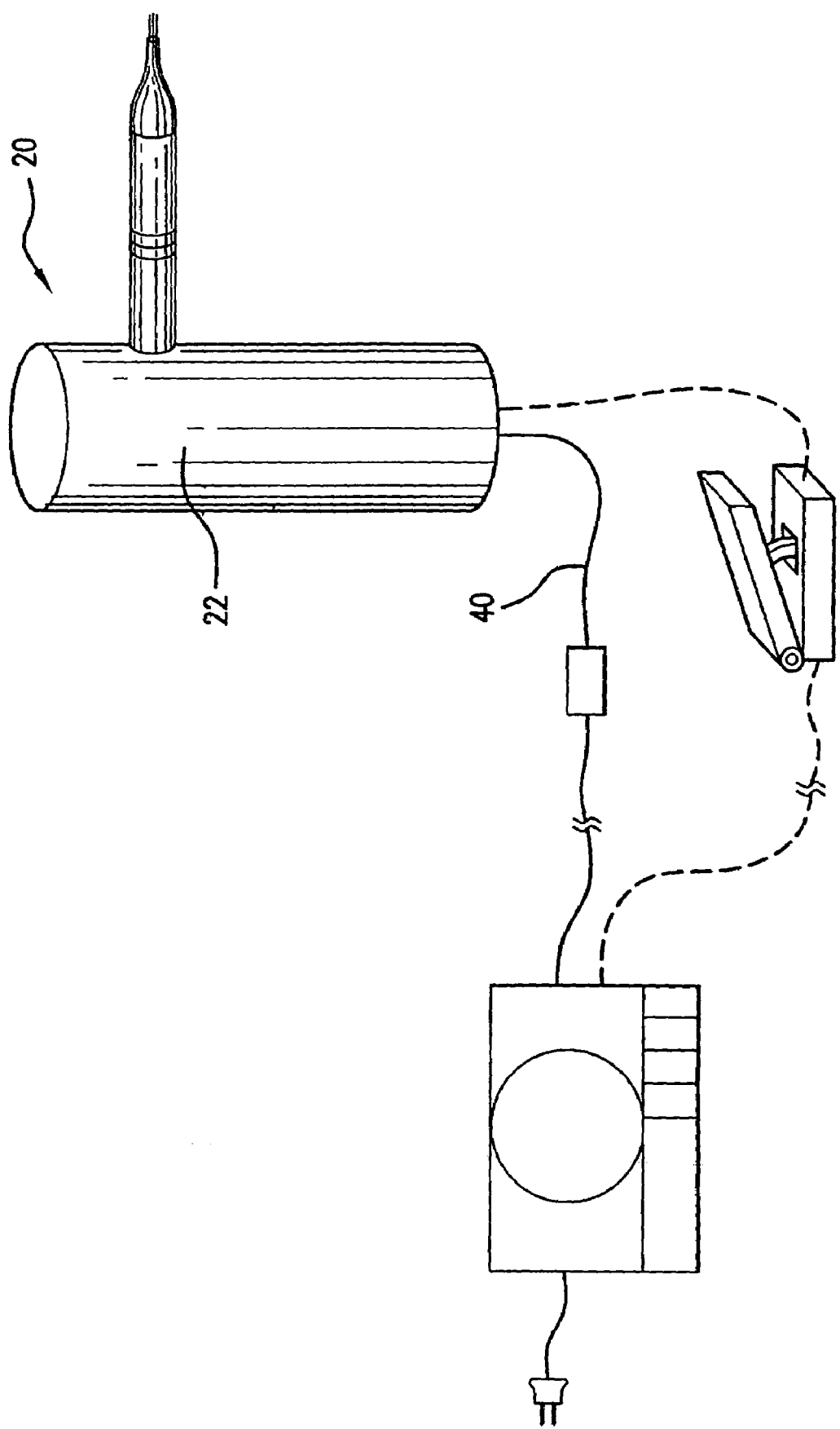
FIG. 10 illustrates a preferred power and speed control arrangement for a motorized intradermal needle injection device featuring a first power-control system.

FIG. 10 illustrates motor driven intradermal device 22 and line cable 40 (either attached or independent of device 22). FIG. 10 illustrates a preferred power and speed control arrangement for a motorized intradermal needle injection device featuring a first power-control system embodiment shown in solid line for providing different reciprocation settings as well as on/off capability. FIG. 10 also illustrates an added foot control for either on/off solely or varying speed by, for example, the number of times the fast control stepped on.

Figure 11:
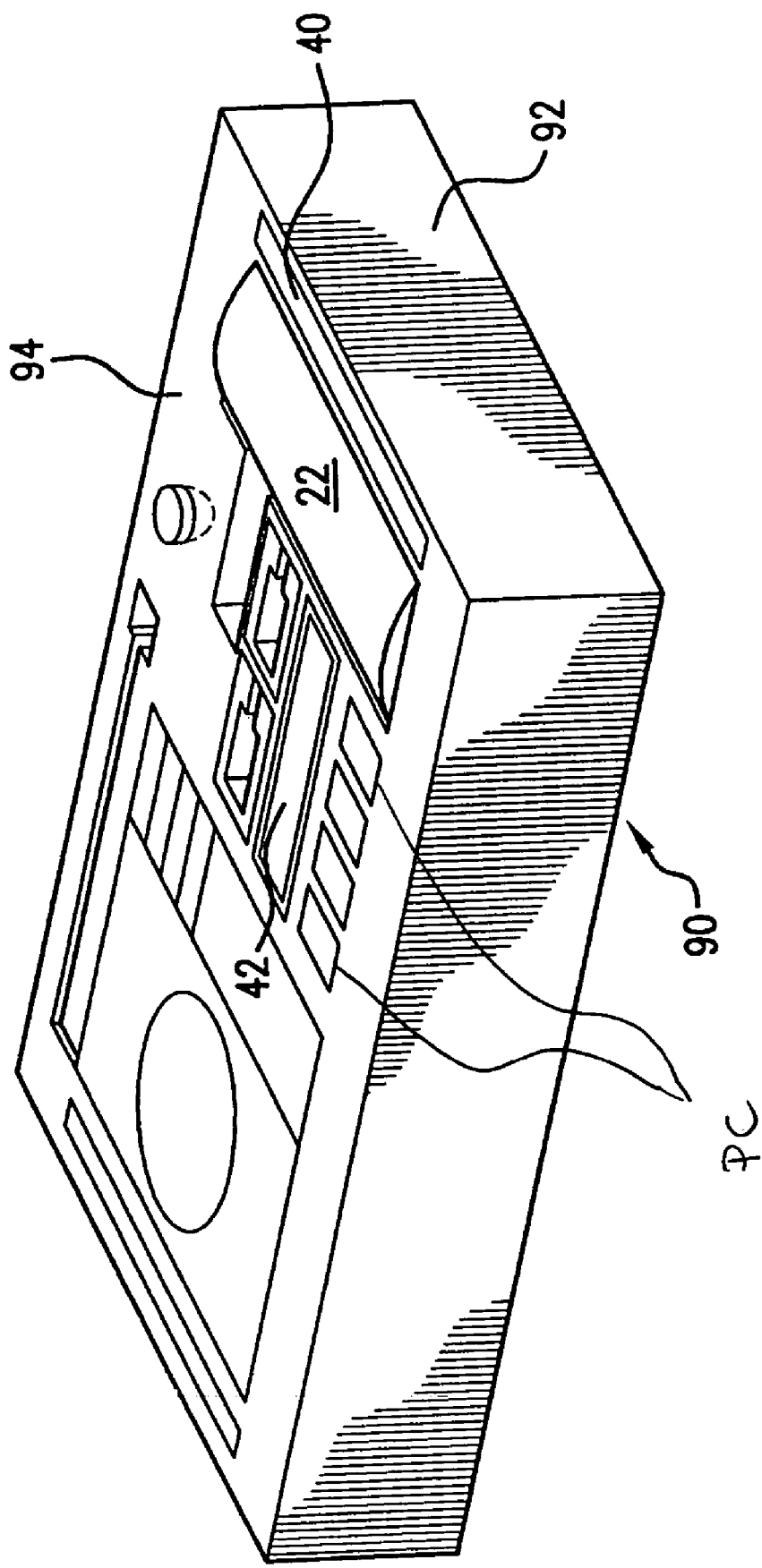
FIG. 11 illustrates an intradermal color introducing needle kit.

FIG. 11 illustrates intradermal color introducing needle kit 90 which is preferably provided in a kit-container 92 in the form of a receiving base having interior filler 94 with reception cavities sized to receive the kit components described above and below. Although not shown, a suitable top or lid if further included.

Figure 12:
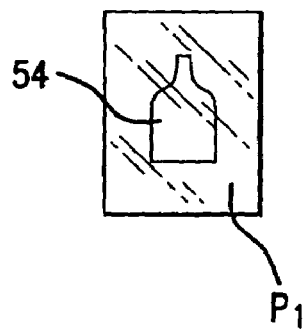
FIG. 12 shows a sealed packet containing a needle tip.
Figure 13:
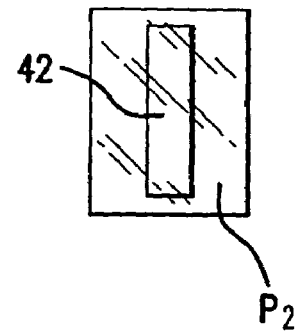
FIG. 13 shows a sealed packet for a disposable sleeve.
Figure 14:
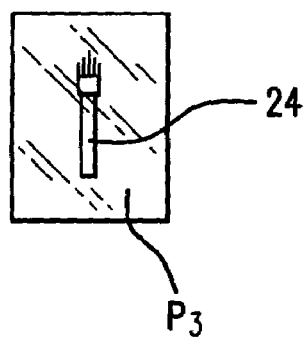
FIG. 14 shows a sealed packet for a needle device.

FIG. 12 shows a sealed packet P1 containing a tip such as tip 54 described above. This tip is designed to be disposable and replaced after each use. Similarly, FIG. 13 shows a sealed packet P2 for a disposable sleeve 42 such that a new, sterile collar in a sealed packet is utilized for each application. Moreover, FIG. 14 shows sealed packet P3 for containing an embodiment of needle device 24. Thus, the needle device of the present invention is also preferably provided in a sealed pack and is disposed of after each use. The kit of FIG. 11 preferably contains a variety of needle pack-cavities PC's which provide storage locations for packets P1 to P3 with the latter preferably being an assorted (color added) collection of packages with different needle configuration and surface edges, etc.

FIGS. 17A and 17B show an alternate embodiment of the needle device 24 of the present invention in high detail with the figures illustrating a needle sub-set arrangement like that shown in FIG. 6A, but with an alternate needle tip morphology. As seen from FIG. 17B there is featured a trocar or multi-sided needle tip in the needle device of FIG. 17A. Thus, rather that tip geometry that is conical, there is illustrated in FIG. 17B a tri-faceted tip that preferably has an irregular surface texture (e.g., coarsely ground). A three face or more or surface trocar arrangement is preferred although two faces or greater than three (e.g., 4 to 8) are also featured under the present invention. The illustrated multi-faceted needle tip geometry is used in conjunction with the above described versatile needle sub-set arrangement and is designed to provide a good compromise amongst the various factors included in providing good color characteristics in the recipient which factors include, for example:

a) an increase in the surface area of the tip so as to carry more color;
    b) a decrease in resistance upon entry into the skin; and
    c) facilitating rapid wound healing (decrease wound healing time) so that walls of the wound are able to close upon themselves easier than a "puncture wound" made by typical pencil-point needles or a similar variations of the same.

In a preferred embodiment rather than the trocar of tri-faceted sharp instruments used to puncture the abdomen for laparoscopy or used in diabetic needles where the edges are very sharp so as to "cut" the skin, the present invention preferably has rounded off or curved or non-two planar bisecting edging. In other words there is provided a good compromise between providing closely positioned, opposing surfaces to facilitate healing while avoiding too extensive a reduction in needle point surface area as well as potential rip edges in the skin puncture. The use of a non-polished or irregular surface areas either relative to the flat "trocar" surface faces, the curved corner edging or both further increases the surface area to provide additional colorant delivery potential. Also the irregular surface feature of the present invention (described above and below) can also be utilized with the above described conical tips to enhance the overall surface area of the needle tip.

The taper of the needle as well as the texture of the needle tip both influence hole size, how much color is able to be carried between and among the needles, in addition to the individual characteristics of the needle. By using, for example, a 3-flat needle set, with a larger central needle to which two needles are soldered on either side, there can be added distance between the needle tips ($\Delta w$).

Thus, the present invention provides for the combination of needles with, for example, two or more different sizes of needles and/or two differently arranged angles in each needle assembly (group) soldered or otherwise joined together, varying textures and tapers of the tips or points of the needles so as to decrease or increase resistance upon entry into the skin, thereby facilitating operator versatility in conjunction with optimal penetration depth. Also, the combinations of needles in accordance with the present invention, make available the providing of maximum needle surface area between and amongst needles so as to hold a maximum amount of the colorant to be delivered beneath the outermost layers of skin. Also, the various combinations and composition of the above needles provide for high quality colorant visibility by the enhancement of color deposition into the skin at the desired depth while also helping to minimize tissue injury, pain and bleeding and thus improve healing and color retention without skin changes such as scarring, prolonged redness or interference by the skins own chromophores (melanin, collagen, connective tissue, vascular supply) due to excessive depth(s) of pigment deposition commonly attained with ordinary needles.

Figure 19:
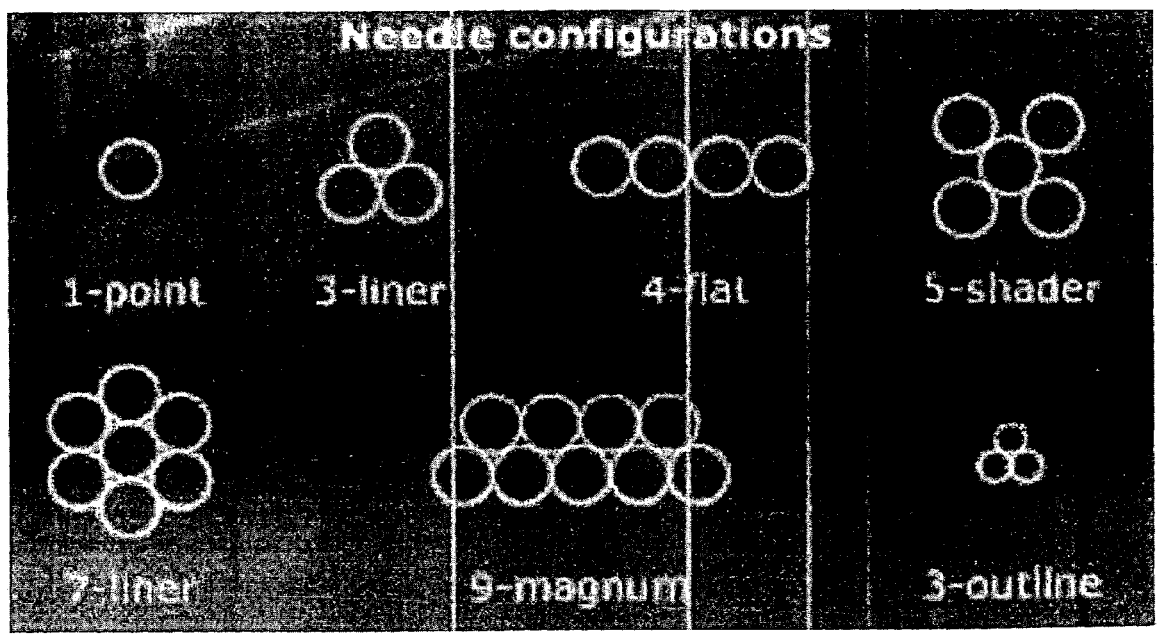
FIG. 19 shows a schematic view of conventional multi-needle groupings.

The present invention's versatility enhancement via, for example, presentment of multiple contact edges or multiple tip height levels, hybrids of different type needles (e.g., gauge or taper or both differences) within a group, variations in tip to tip width spacing ($\Delta w$), needle point morphology (trocar) and/or surface characteristics (e.g. irregular pocked, ridged or non-smooth coatings), provides for alternate arrangements as to other needle device FIG. 19 illustrates some conventional needle configurations used in tattooing which all feature the same needle type and a single plane or edge needle point or tip arrangement. As shown in FIG. 19, in addition to a single plane or "flat" embodiment there are also various cluster arrangements. The features of the present invention also provide for versatility with respect to non-flat and non-flat matrix stack embodiments, including, for example, 3 to 12 point clusters featuring a central needle surrounded along a circumferential with additional needles or a tri-point arrangement featuring three needles with each touching two adjacent neighbor needles. Examples of different level point arrangements include, for example a central needle extending out to a different level than the needles attached to it (either directly as in a weld or via an intermediate support).

Figure 28A:
FIG. 28A shows a cut-away view of a three point needle cluster of fine gauge needles (or a portion of a five point needle cluster).
Figure 28B:
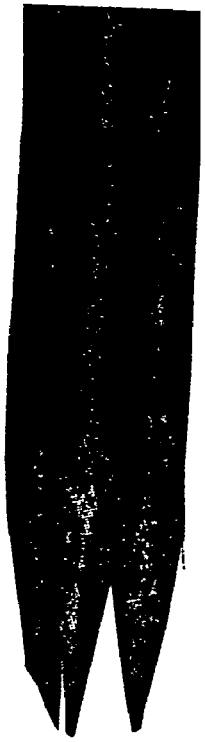
FIG. 28B shows a cut-away view of a three point needle cluster of a larger gauge needle than in FIG. 28A (or a portion of a five point needle cluster).

FIGS. 28A and 28B are illustrative of a tri-point arrangement as in the 3-outline (all fine needles at same distance out) and the 3-liner (all larger diameter needles at same distance out) shown in FIG. 19 (and are also partially illustrative of a 5 point arrangement as in the 5 shader shown in FIG. 19).

Figure 28C:
FIG. 28C shows a cut-away partial view of a portion of a five point needle cluster having a larger gauge central needle and a smaller gauge needle group circumferentially spaced about the central needle.
Figure 28D:
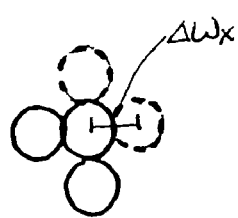
FIG. 28D shows a schematic view of the needle cluster of FIG. 28A with five points.
Figure 28E:
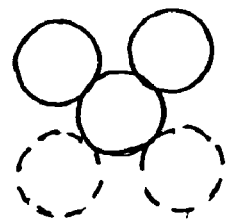
FIG. 28E shows schematic view of the needle cluster of FIG. 28B with five points.
Figure 28F:
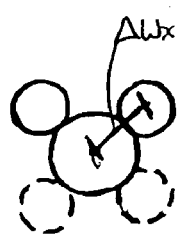
FIG. 28F shows a schematic view of the needle cluster of FIG. 28C with five points.

FIG. 28C illustrates an embodiment of the present invention featuring altering types of needle types (e.g., different diameter gauge) showing two finer attached to a larger grade needle in a three point arrangement. FIGS. 28D, E and F show the aforementioned expansion in number to a 5 point needle type with 28D and 28E showing fine and less fine gauge sets, respectively, and FIG. 28F showing a hybrid arrangement in accordance with the present invention featuring a central large diameter needle surrounded by a plurality of circumferentially arranged finer needles (4 finer in the illustrated instance—with two in dash lines showing the expansion from the embodiment of FIG. 28C). As seen from a comparison of FIGS. 28D and 28F, by including the larger diameter central needle, there is increased the relative spacing width ($\Delta wx$) for the fine needles alone to ($\Delta wx'$) for the hybrid arrangement. This expansion provides additional ink pick up surface area and capillary volume, while still maintaining a fine needle characteristic for the needle usage.

Figure 18A:
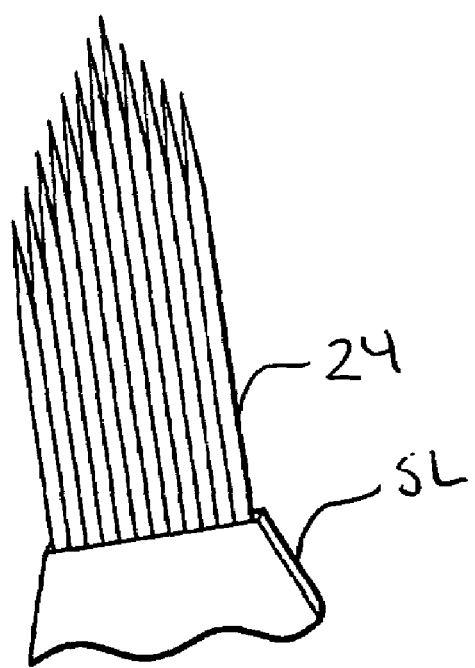
Figure 18B:
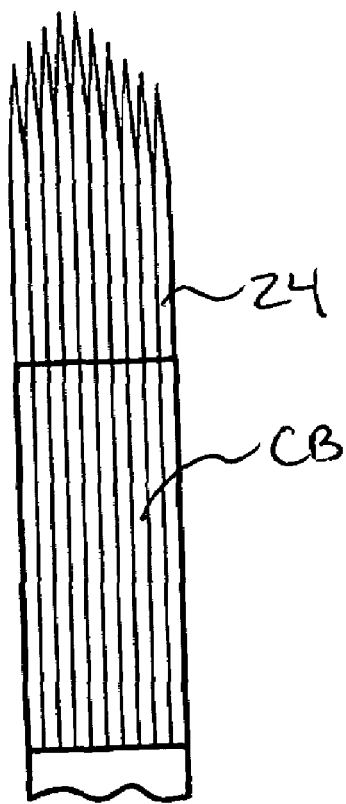

A desired degree of spacing can also be achieved by way of a spacing ring such as the ring RI illustrated in FIG. 26A which provides increased $\Delta w$ spacing and also facilitates proper positioning of the circumferentially positioned needles as presented in FIG. 26A. A metal ring which can facilitate a weld or solder bond is featured under the present invention as a spacing ring. The aforementioned FIGS. 18A and 18B also illustrate alternate forms of needle retention means as in the sleeve SL in FIG. 18A and the clamping band CB in FIG. 18B (used with or without solder or adhesive)

FIG. 20 illustrates an alternate embodiment for a needle tip of the present invention which has a four face trocar configuration (four faces as compared to the three faces of the FIG. 17B). This arrangement facilitates rapid and less traumatic intradermal insertion while still presenting relatively large surface area presentation via its multiple faces. FIG. 28A shows a schematic illustration of the needle puncture area PA within the skin I of a person. Unlike a circular puncture produced by a conical needle configuration where there is a maximum opposing point spacing, the trocar puncture area PA shows opposing walls relatively close to each other to facilitate a rapid healing (as compared to the circular puncture which is similar to stepping on a nail which puncture is an example of a slow to heal cavity). In other words with a conical puncture healing only takes place in bottom up fashion as the conical hole changes from the bottom taper up with the puncture pattern of 20A and 21A there is provided the ability of healing relative to the opposing walls such as with initiation of the closely positioned corners (sharp or the below described rounded edge embodiment).

The sharp edge trocar puncture shown in FIG. 20A does represent a reduction in surface area penetrating the skin as compared to a conical needle and thus an alternate embodiment of the invention features a compromise arrangement featuring a partial trocar with easily penetrating sloped face walls (either planar or curving in or out face walls—such as illustrated by an internally blown up umbrella with expanded convex surfaces between bordering framing/edging), together with rounded trocar face edges. In this regard reference is made to FIGS. 21 and 21A with the former illustrating an embodiment featuring trocar faces TF and rounded border edging RE extending the full axially length of the side edges of the faces. FIG. 21A illustrates the puncture pattern for the trocar needle tip of FIG. 21 (it being noted that the axial length of the illustrations can be short as shown but is also often typically longer relative to the diameter as in the conical configuration range of taper length discussed above). The puncture pattern in FIG. 21A illustrates an opposing wall pattern to promote healing and a rounded edging pattern which provides greater surface area and lessens the potential for intradermal tearing at a puncture edge.

FIG. 22 shows an alternate embodiment of the present invention which includes an irregular surface area pattern on the faces (also can be on the rounded surfaces alone or a combination of the same) as, for example, course grind pockets, scratches or recesses extending below the plane of the trocar face. FIG. 22A provides a closer view of such pockets or recesses which can also be formed by chemical etching or alternate removal processes wherein material is randomly or non-randomly removed from areas presented by the faces of the trocar tip. This irregular surface with depressions DE provides both increased overall surface area but also potential pooling locations for adhered ink.

FIG. 23 shows a similar embodiment as to the trocar with rounded edges but with a protrusion pattern PR extending up from the trocar point surface (e.g., the trocar faces or the trocar rounded corner edges or both). A variety of techniques for adding such surface protrusions is possible such as metal depositing techniques (e.g., charged deposit techniques where a fine particle spray at one charge is introduced into the area around an oppositely charged needle tip)

FIG. 27 shows an additional embodiment for enhancing surface area of the needle tip (trocar in this instance) wherein the needle tip of FIG. 20 is dipped in a material as in a molten material as in metal which coats the tip in an uneven manner to leave a coating comprised of depressions and/or projections along the exterior surface of the coating (gas injection to form dispersed gas bubbles can further increase surface area upon release during drying and the formation of residue pockets. The bond should be sufficient to avoid the potential for flaking and the pockets or contours should be designed to provide enhanced surface area while avoiding an undesired increase in skin trauma (e.g. use of smooth wall projections and/or recesses).

As described in the background section of the present application, an additional feature involved in providing quality coloring is avoiding either too shallow or too deep the needle penetration. FIGS. 24 and 25 illustrate some penetration controlling means as in the expanded wedge shape (or conical as in an umbrella tip configuration if a single or only a few needles are involved as opposed to a flat arrangement with multiple needles were upon the wedge configuration provides for flat plane extension with the needle row). The needle point and base are shown broken away to illustrate the depth is variable depending on desired usage and associated penetration.

FIG. 25 illustrates a yoke collar arrangement (e.g. an oval shaped ring for an extended flat set) which is positioned to block too deep a penetration as described above. The yoke also provides a means to retain together the needle set. It can also be designed to conform to a different oblique orientation as in an angled applied or molded on conforming angled section in the oval ring.

To fix needles into a needle device, the needles are preferably positioned in a mold or die and fixed by a fixing operation such as the application of fixing means which can be mechanical clamping arrangement (e.g., a cylindrical sleeve in the case of a cluster arrangement with or without interior soldering or welding or a wrap) but more preferably the obtainment of an interjoining material relationship such as applying a solder coating and/or adhesive coating alone while the relative needle relationship is maintained after having been achieved.

To facilitate providing the desired needle point surface morphology, the present invention also features a needle grinding machine GM for multi-facetted needles as in a automatic or semi-automatic needle grinding (hereafter "SANG Machine" for convenience) which is preferably adapted for working with (standard) for 300 or 400 series stainless steel wire with the following characteristics

| Diameter | .014"-.080" (0.35-2.0 mm) |
| Length between | .75" and 2" (19-50 mm) | or an extension of the same with modified tooling.

Figure 29:
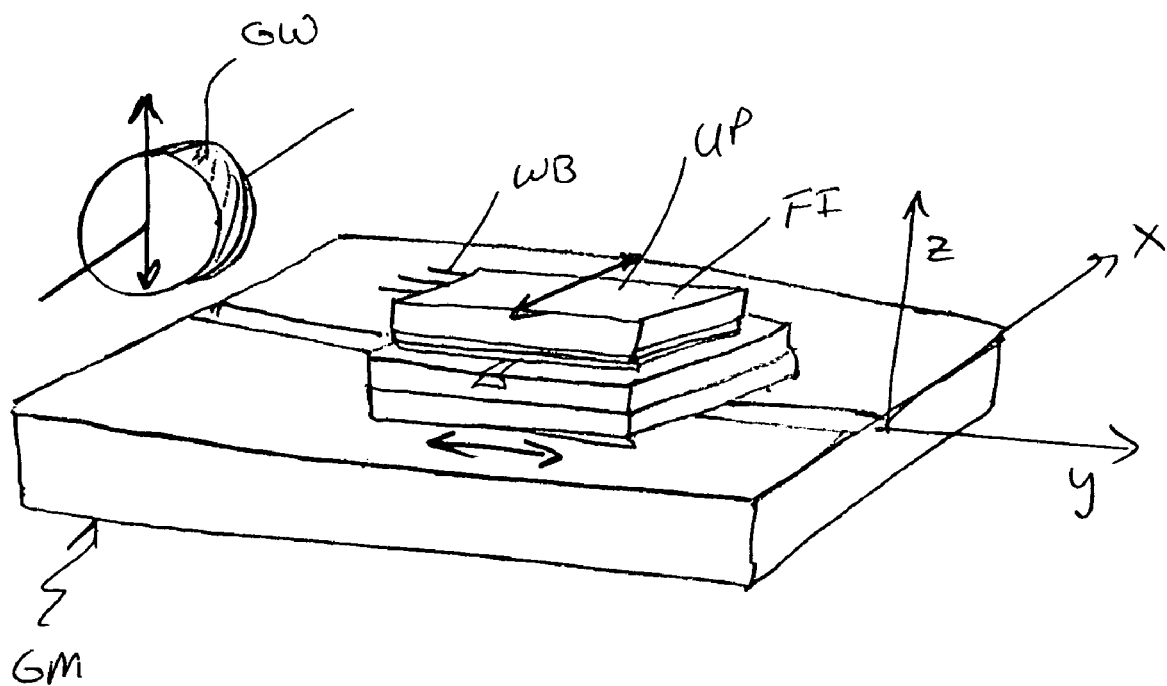
FIG. 29 shows a view of a machine for forming multi-faceted (e.g., trocar) needle with surface texture.

The modular machine design shown in FIG. 29 can be used for a variety of different applications (lancets, trocar, hypodermic needles, etc.) and has particular utility in the production of the above described low trauma/high surface area with large volume ink retention and application needle points.

As represented schematically in FIG. 29, the SANG machine preferably comprises an automatic grinding cycle for each facet as well as a preferred dry grinding with CBN grinder wheel and optional wet grinding with automatic or manual loading of wire blanks WB into fixture FI and the unloading of finished needles as carried out either manually or in a automatic fashion. As shown in FIG. 29, fixture FI has a movable (x-axis) upper plate relative to a fixed x-axis lower plate and a supporting elastomeric pad; such that movement of the upper plate along the x-axis causes rotation of the wire blanks WB. Plunging of blanks WB is preferably carried out by moving fixture FI in the Y-axis direction (and/or grinder) into and out of contact with the grinding wheel GW (e.g., a three plunge operation to remove needle point material in stages until the surface contour is achieved (e.g., trocar face)).

There is also optionally included a micro blasting station with beed collector which can be used for added surface texturing.

In a preferred embodiment, grinding the needle tips is carried out with a cylindrical grinding wheel of approximately 4"-6" in diameter and 3" wide. This diameter will be reflected in the geometry of the facets. In a preferred embodiment all needles are lined up parallel in 4" wide clamping fixtures. The fixture is made adjustable (and/or the grinding wheel support), as in a shift of the needles to the left and to the right by way of a rubber or high friction retention surface and relative shifting of above/below plates to cause a desired degree of rotation in the needle blanks there between. In this way it is possible to grind multiple facets, to provide for the multi-faceted grinding of the blanks tip and by rotation and/or relative grinder plunge relationship, formation of the rounded corner edging can also be carried out.

The blanks from which the needles are to be formed are preferably cleaned of oil and any contamination before feeding them into the grinder. Good straightness and burr free, square cuts are desirable for the subsequent grinding operation.

The loading and unloading of blanks/needles preferably involves automated or manual loading of the needle blanks into the grinding fixture. The fixture is preferably released secured to its underlying (movable) support and thus can be taken out of the machine for loading/unloading. A special jig is provided to pre-sort the needles and to facilitate the loading process. The grinding fixture preferably holds about 150-200 needles and the blanks are preferably lined up parallel in horizontal plane and with their butt end against a stopper is a preferred production method under the present invention.

At the end of the grinding cycles, the operator (or a means for removing) as in a pushed mechanism) takes the fixture out of the machine and unloads the finished needles.

In a preferred embodiment, the machine is equipped with one grinding station and a horizontal slide with motorized axis control for the feed movement (plunge grinding). The grinding station has a manual slide movement in z-axis (up/down) with micro meter adjustment. This movement allows for adjusting to different needle tip taper angles. The fixtures are designed to shift the needles (e.g., left or right) to grind additional facets (e.g., the second and third facet) to the required angle and/or the rounded edges between facets. The shifting is done manually or automatically preferably after each grinding cycle. The needle tips can also be ground in several passes (pecks). The machine control allows the programming of the number of passes and the feed rate.

The grinding wheel is preferably a CBN type wheel. The wheel grid has to be selected in accordance with the required needle tip surface finish (texture). A grid size (FEPA, P-scale) of 20 to 80, more preferably 40 to 60, is used in one embodiment of the invention to provide relatively coarse grinding which leaves a textured surface in the needle tip (scratches that provide increased surface area and ink retention) Thus, under the present invention, a decision is made as to the level of coarseness to be provided in the needle point taking in consideration that increased coarseness provides increased surface area and ink retention capability which potentially increases intradermal insertion resistance as compared to a polished needle (with the latter providing a poor level of ink retention).

The present invention also includes a method of forming multi-faceted and/or increased area surface texture by utilizing the grinding system described above.

Also, the cycle time for the grinding machine depends on the particular application, but the grinding of each facet takes only 1 to 5 seconds under a preferred rpm level, as compared to a manual loading/unloading which takes a few minutes.

The SANG Machine also preferably includes a Machine control processor and a touch screen as in one having the following functions for:

Start/Stop
Spindle On/Off
Max. spindle rpm lock out function
Jog/Automatic cycle
No. of pecking cycles
Pecking positions
Feed rates The control preferably comprises a
GE Fanuc control model 90-30 with touch screen
230 Volt, 50 or 60 cycles, 3 phases, 20 Amp.
Control voltage 24 Volt DC.

Compressed air is provided for remaining removal material such as a 100 psi line pressure, filtered and oil free The machine can also be equipped with nozzles mounted next to the grinding wheels to extract the grinding dust. These nozzles have to be connected to a central vacuum system. A freestanding self-contained vacuum system is also an option.

It should be emphasized that the above-described embodiments of the present invention, particularly, and "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of the disclosure and the present invention and protected by the following claims.

What is claimed is:

1. A needle device for use in intradermal coloring, comprising:
    a set of intradermal color introduction needles, with the needles of said set having axes of elongation falling on a common plane and each of said needles having a pointed application end, said set of needles including a first sub-set of needles with pointed application ends arranged along a first contact edge and a second sub-set of needles with pointed application ends arranged along a second contact edge that is non-coincident with the first contact edge, and wherein at least one intermediate positioned needle extends out farther than a less intermediate positioned needle within the set.

2. The device of claim 1 wherein said first contact edge is arranged along a horizontal line when said needle device is vertically oriented.

3. The device of claim 2 wherein said second contact edge extends obliquely relative to said first contact edge arranged along the horizontal line.

4. The device of claim 3 wherein said second contact edge defines an angle of 10° to 60° relative to the horizontal line.

5. The device of claim 4 wherein said angle is from 20° to 50°.

6. The device of claim 4 wherein said angle is from 30° to 45°.

7. The device of claim 1 wherein said first sub-set of needles presents a different number of needle points along the first contact edge relative to the second contact edge.

8. The device of claim 7 wherein said first contact edge is arranged along a horizontal line and said second contact edge extends obliquely up away from said horizontal line and has a greater number of needle points than the needle points defining said first contact edge.

9. The device of claim 8 wherein a ratio range of needle points of said second contact edge relative to said first contact edge is 2/1 to 6/1.

10. The device of claim 1 wherein said first contact edge extends obliquely up and away from a horizontal reference plane and said second contact edge extends obliquely up and away from the horizontal plane.

11. The device of claim 10 wherein said second contact edge presents 8 needle tips and said first contact edge presents 2 needle tips with each contact edge inclusive of a shared needle point.

12. The device of claim 1 wherein said first and said second contact edges share a common single needle point edge representing a vertex of an angle defined by said obliquely oriented first and said second contact edge.

13. The device of claim 1 wherein said first and said second contact edges have a different number of needle points.

14. The device of claim 1 wherein the needle points of the first and said second contact edges are in a ratio of 1.5/1 to 3/1.

15. The device of claim 14 wherein the number of needle points defining said first contact edge is 8 and the number of needle points defining said second contact edge is 4 with each inclusive of a common vertex needle point.

16. The device of claim 1 wherein adjacent needles in said needle set are fixed together and lie in a common plane.

17. The device of claim 16 wherein said needles are fixed together at the non-application ends of said needle set, and free ends of said non-application ends lie along edge lines that are parallel to first and second contact ends.

18. The needle device of claim 1 further comprising a third sub-set of needles having pointed application ends arranged non-coincident with respect to said first and second contact edges.

19. The device as recited in claim 18 wherein said first contact edge is arranged along a horizontal line, said second contact edge extends obliquely up away from the horizontal line to one side of said first contact edge and said third contact edge extends obliquely from the horizontal line to a second side of said first contact edge.

20. The device as recited in claim 19 wherein said second and said third contact edges having different slope angles.

21. The device as recited in claim 20 wherein said second and said third contact edges have at least a 10° difference.

22. The device as recited in claim 21 wherein said second contact edge has a 30° angle and said third contact edge has a 45° angle.

23. The device as recited in claim 18 wherein said first contact edge extends along a horizontal line, said second contact edge extends obliquely from a common needle point with said first contact edge and said third contact edge has a different slope than said second contact edge.

24. The device of claim 18 wherein at least two of said first, said second and said third contact edges present a different number of needle points.

25. The device of claim 18 wherein at least two of said first, said second and said third contact edges are defined by needles of a different grade.

26. The device of claim 25 wherein each of said first, said second and said third contact edges are defined by needles of a different grade.

27. A colorant implement apparatus, comprising:
    the needle device of claim 1; and
    a tool to support said needle device.

28. The apparatus of claim 27, wherein said tool includes means for reciprocating said needle device.

29. A method of providing intradermal coloring to a recipient, comprising:
    supplying colorant to a needle device which comprises a set of needles, with the needles of said set having axes of elongation falling on a common plane and each of said needles having a pointed application end, said set of needles including a first sub-set of needles with pointed application ends arranged along a first contact edge and a second sub-set of needles with pointed application ends arranged along a second contact edge that is non-coincident with the first contact edge; and
    penetrating a skin region of the recipient to alter coloring of the skin region.

30. A needle device, comprising:
a set of needles, with the needles of said set having axes of elongation falling on a common plane and each of said needles having a pointed application end, said set of needles including a first sub-set of needles with pointed application ends arranged along a first contact edge and a second sub-set of needles with pointed application ends arranged alone a second contact edge that is non-coincident with the first contact edge; and
wherein said first and said second sub-sets of needles are of different grades.

31. The device of claim 1 wherein one of said first and said second sub-sets has a finer taper than the other of said first and said second sub-sets.

32. The device of claim 31 wherein said finer taper sub-set of needles has a smaller shaft diameter than said other of said first and said second sub-sets.

33. A needle device for use in intradermal coloring, comprising:
a set of intradermal color introduction needles, with the needles of said set having axes of elongation falling on a common plane and said set of needles being arranged in a first and a second sub-set of needles with the first sub-set having a plurality of needle points arranged along a first line of extension and said second sub-set having a plurality of needle points arranged along a second line of extension non-coincident with said first line of extension, and wherein said first and second lines of extension converge toward an outermost free end of said needle set.

34. The device of claim 33 wherein each of said first and said second lines of extension are oblique relative to a horizontal reference plane when the needle device is in a vertical orientation.

35. The device of claim 34 wherein the needles of said first sub-set are different in configuration than that of said second sub-set.

36. The device of claim 34 wherein the number of needle points in said first sub-set is different than that in said second sub-set.

37. The needle device of claim 34 wherein said first line of extension is horizontal and said second line of extension oblique relative to the first line of extension and said second line is defined by a greater number of needle points than that of said first sub-set.

38. The needle device of claim 37 wherein the needle points of said second sub-set has a sharper taper than that of said first sub-set.

39. A needle device for use in intradermal coloring, comprising:
a plurality of intradermal color introduction needles arranged in a common plane and fixed in relationship to each other, said needles presenting needle points arranged at different distances from a reference horizontal plane contacting an outermost, free end needle point of said plurality of needles, and
the relative distances of said needle points being set so as to provide at least two different non-coincidental needle tip contact edges, and wherein said first contact edge is a straight edge extending along the reference plane and said second contact edge extends obliquely away from said first contact edge and has a greater number of needle points than that of the first contact edge, which edges diverge in going from the outermost needle point toward the reference horizontal plane.

40. The device of claim 39 wherein three different non-coincident edges are provided with two of said three different contact edges diverging in a direction going out away from the reference plane.

41. The device of claim 39 including a straight edge and two oblique edges.

42. A method of forming a needle device, comprising:
providing a number of individual needles in a side-by-side orientation in a die;
adjusting the die so as to present an oblique line of needle points arranged on a first contact edge and one other non-coincident line of needle points representing a second contact edge, with the axes of elongation of the needles defining said first and second contact edges lying in a common plane; and
fixing the needles in position relative to each other following adjusting the die.

43. A needle device for use in intradermal color introduction comprising a set of intradermal color introduction needles each having a pointed application end, said set of needles defining a non-linear contact edging pathway, which is suited for skin contact manipulation by the user, extending between a leftmost end needle and a rightmost end needle relative to a common plane defined by said needle set, and wherein the leftmost needle of said non-linear contact edging pathway suited for skin contact manipulation extends out a different length relative to the rightmost end needle suited for skin contact manipulation and wherein an intramediate one of said needles falling between said leftmost and rightmost needles extends out farther than at least one of said leftmost and rightmost needles.

44. A needle device as recited in claim 43 wherein said needle set includes a plurality of needles that are multi-faceted and have increased area surface texture.

45. The needle device as recited in claim 44 wherein said needle points are trocar points.

46. The needle device as recited in claim 45 wherein edges between trocar faces are rounded edges extending for at least 5% of an overall circumference extending along the edges.

47. The needle device of claim 43 wherein said non-linear contact edging is defined by a plurality of contact edges which each contain a first subset of needles with pointed application ends arranged along a first contact edge and a second subset of needles with pointed application ends arranged along a second contact edge that is non-coincident with the first contact edge.

48. The needle device as recited in claim 43 wherein said needle set includes an extension needle extending farther than all other needles in said set, with said extension needle being non-centered within said set of needles relative to a common plane for said set of needles.

49. The needle device as recited in claim 48 wherein said extension needle is positioned between the leftmost needle and a center location of said needle set relative to said common plane.

50. The needle device of claim 43 wherein said non-linear contact edging is relative to an overall left to right non-linear contact edging pathway extending from the leftmost end needle to a rightmost end needle, and wherein said non-linear contact edging pathway is defined by a plurality of linear contact edge segments which comprise a first sub-set of needles with pointed application ends arranged along a first linear contact edge and a second sub-set of needles with pointed application ends arranged along a second linear contact edge that is non-coincident with the first contact edge.

* * * * *